(12) United States Patent
Meltzer et al.

(10) Patent No.: US 7,026,516 B2
(45) Date of Patent: Apr. 11, 2006

(54) COMPOUNDS WITH HIGH MONOAMINE TRANSPORTER AFFINITY

(75) Inventors: Peter C. Meltzer, Lexington, MA (US);
Paul Blundell, Winchester, MA (US);
Pinglang Wang, Cambridge, MA (US);
Bertha K. Madras, Newton, MA (US)

(73) Assignees: President and Fellows of Harvard College, Cambridge, MA (US);
Organix, Inc., Woburn, MA (US)

( * ) Notice: Subject to any disclaimer, the term of this patent is extended or adjusted under 35 U.S.C. 154(b) by 0 days.

(21) Appl. No.: 10/374,892

(22) Filed: Feb. 24, 2003

(65) Prior Publication Data

US 2004/0014992 A1    Jan. 22, 2004

Related U.S. Application Data

(63) Continuation-in-part of application No. 09/691,396, filed on Oct. 17, 2000, now Pat. No. 6,525,206, and a continuation-in-part of application No. PCT/US01/32575, filed on Oct. 17, 2001.

(60) Provisional application No. 60/401,836, filed on Aug. 6, 2002.

(51) Int. Cl.
*C07C 43/02* (2006.01)
(52) U.S. Cl. .................. 568/626; 558/303; 544/106
(58) Field of Classification Search ............... 558/303; 568/626; 544/106
See application file for complete search history.

(56) References Cited

FOREIGN PATENT DOCUMENTS

WO    WO 98/06689    2/1998

OTHER PUBLICATIONS

Acton, et al., "Single-Photon Emission Tomography Imaging of Serotonin Transporters in the Nonhuman Primate Brain With [$^{123}$I]ODAM," European Journal of Nuclear Medicine, 26:1359-1362 (1999).
Basaif, et al., International Journal of Chemistry, 6:55-65 (1995) (XP002209431)—Abstract.
Biederman, M.D., "Attention-Deficit/Hyperactivity Disorder: A Life Span Perspective," J. Clin. Psychiatry, 59:4-16 (1998).
Bogeso, et al., "3-Phenyl-1-Indanamines. Potential Antidepressant Activity and Potent Inhibition of Dopamine, Norepinephrine, and Serotonin Uptake," J. Med. Chem., 28:1817-1828 (1985).
Breslow, et al. Journal of Organic Chemistry, (XP002209567), 26:679-681 (1961).
Canfield, et al. "Autoradiographic Localization of Cocaine Binding Sites by [$^3$H]CFT ([$^3$H]WIN 35,428) in the Monkey Brain," Synapse, 6:189-195 (1990).
Corson, et al., Journal of Organic Chemistry (XP002209566), 27:1636-1640 (1962).
Coyle, et al., "Catecholamine Uptake by Synaptosomes in Homogenates of Rate Brain: Stereospecificity in Different Ares," The Journal of Pharmacology and Experimental Therapeutics, vol. 170 (1969).
Cyr, et al., "Current Drig Therapy Recommendations for the Treatment of Attention Deficit Hyperactivity Disorder," Drugs, 56:215-223 (1998).
Ficini, "Laborratoire de Chimie Structurale, Faculte des Sciences; Paris," 5$^e$, pp. 119-124 (1956).
Fischman, et al., "Rapid Detection of Parkinson's Disease by SPECT With Altropane: A Selective Ligand for Dopamine Transporters," 29:128-141 (1998).
Gehlert, et al., "The Selective Norepinephrine Reuptake Inhibitor, LY368975, Reduces Food Consumption in Animal Models of Feeding," The Journal of Pharmacology and Experimental Therapeutics, 287:127 (1998).
Ghosh, et al., Tetrahedron Letters, 41:8425-8429 (2000).
Giros, et al., "Hyperlocomotion and Indifference to Cocaine and Amphetamine in Mice Lacking the Dopamine Transporter," Nature, 379:606-612 (1996).
Hadrich, et al., "Synthesis and Characterization of Fluorescent Ligands for the Norepinephrine Transporter: Potential Neuroblastoma Imaging Agents," J. Med. Chem., 42:3101-3108 (1999).
Heinz, et al., "Reduced Central Serotonin Transporters in Alcoholism," American Journal of Psychiatry, 155:1544-1549 (1998).
Hirschfeld, M.D., "Care of the Sexually Active Depressed Patient," J. Clin. Psychiatry, 60:32-35 (1999).
Jorenby, et al., "A Controlled Trial of Sustained-Release Bupropion, a Nicotine Patch, or Both for Smoking Cessation," The New England Jounal of Medicine, 340:685-691 (1999).

(Continued)

*Primary Examiner*—Kamal A. Saeed
(74) *Attorney, Agent, or Firm*—George W. Neuner, Esq.; Edwards Angell Palmer & Dodge LLP

(57) ABSTRACT

Featured compounds have high monoamine transport affinity and are characterized by one of the following two general formulas set out above. The compounds bind selectively or non-selectively to monoamine transporters. The compounds are useful to treat various medical indications including attention deficit hyperactivity disorder (ADHD), Parkinson's disease, cocaine addiction, smoking cessation, weight reduction, obsessive-compulsive disorder, various forms of depression, traumatic brain injury, stroke, and narcolepsy.

9 Claims, 6 Drawing Sheets

OTHER PUBLICATIONS

Kaufman, et al., "Severe Depletion of Cocaine Recognition Sites Associated with the Dopamine Transporter 1 Parkinson's Diseased Striatum," Synapse, 9:43-49 (1991).

Kung, H.F., "Synthesis of New Bis(aminoethanethiol) (BAT) Derivatives: Possible Ligands for $^{99m}$Tc Brain Imaging Agents," J. Med. Chem. 28:1280-1284 (1985).

Madras, et al., "Cocaine Receptors Labeled by [$^{3}$H]2β-Carbomethoxy-3β-(4-fluorophenyl)tropane," Molecular Pharmacology, 36:518-524 (1989).

Madras, et al., "Technepine: A High-Affinity $^{99m}$Technetium Probe to Label the Dopamine Transporter in Brain by SPECT Imagine," Synapse, 22:239-245 (1996).

Madras, et al., "Nitrogen-Based Drugs Are Not Essential for Blockade of Monoamine Transporters," Synapse, 24:240-248 (1996).

Malison, et al., "Reduced Brain Serotonin Transporter Availability in Major Depression as Measured by [$^{123}$I]- 2β-Carbomethoxy-3β-(4-Iodophenyl)tropane and Single Photon Emission Computed Tomography," Biological Psychiatry, 44:1090-1098 (1998).

McAfee, et al., "Sustained Release Bupropion for Smoking Cessation," New England Journal of Medicine, 338:619 (1998).

McCann, U.D., "Positron Emission Tomographic Evidence of Toxic Effect of MDMA ("Ectstasy") on Brain Serotonin Neurons in Human Beings," The Lancet, 352:1433-1437 (1998).

McOmie, et al., Tetrahedron, (XP000567035) 24:2289-2292 (1968).

Muller, et al., Journal of Organic Chemistry, 16:1003-1024 (1950).

O'Neil, et al., "Preparation and Structural Characterization of Monoamine-Monoamide Bis(thiol) Oxo Complexes of Technetium (V) and Rhenium(V)," Inorganic Chemistry, 33:319-323 (1994).

O'Neil, et al., "Progestin Radiopharmaceuticals Labeled with Technetium and Rhenium: Synthesis, Binding Affinity, and in Vivo Distribution of a New Progestin $N_2S_2$-Metal Conjugate," Bioconjugate, 5:189-193 (1994).

Oya, et al., "A New Single-Photon Emission Computed Tomography Imaging Agent for Serotonin Transporters: [$^{123}$I]IDAM, 5-Iodo-2-((2-((dimethylamino)methyl)-phenyl)thio)benzyl Alcohol," Journal of Medicinal Chemistry, 42:333-335 (1999).

Raffel, et al., "Influence of Vesicular Storage and Monoamine Oxidase Activity on [$^{11}$C]Phenylephrine KInetics: Studies in Isolated Rat Heart," The Journal of Nuclear Medicine, 40:323-330 (1999).

Riggs, et al., "An Open Trial of Bupropion for ADHD in Adolescents with Substance Use Disorders and Conduct Disorder," Journal of the American Academy of Child and Adolescent Psychiatry, 37:1271-1278 (1999).

Seeman, et al., "Anti-Hyperactivity Medication: methylphenidate and Amphetamine," Molecular Psychiatry, 3:386-396 (1998).

Seibyl, et al. "Decreased Single-Photon Emission Computed Tomographic [$^{123}$I]β-CIT Striatal Uptake Correlates with Symptom Severity in Parkinson's Disease," Annals of Neurology, 38:589-598 (1995).

Semple, et al., "Reduced In Vivo Binding to the Serotonin Transporter in the Cerebral Cortex of MDMA ('ecstacy') Users," The British Journal of Psychiatry, 175:63-69 (1999).

Szabo, et al., "Kinetic Analysis of [$^{11}$C]McN5652: A Serotonin Transporter Radioligand," Journal of Cerebral Blood Flow and Metabolism, 19:967-981 (1999).

Walter, et al., Journal of Medicinal Chemistry, (XP002209564) 17:459-463 (1974).

Zwiebrak, et al., Journal of Organic Chemistry, (XP002209563) 28:3392-3399 (1963).

Scheme 1

2-Naphthyl Analogues

12

Scheme 3

Scheme 4

Scheme 5.

<sup>a</sup>Reagents: (i) *t*-BuOK, cycloalkylbromide; (ii) HCl, MeOH

COMPOUNDS WITH HIGH MONOAMINE TRANSPORTER AFFINITY

RELATED APPLICATIONS

This application is a continuation-in-part of U.S. application Ser. No. 09/691,396, filed Oct. 17, 2000, now U.S. Pat. No. 6,525,206, and is a continuation-in-part of PCT Application No. PCT/US01/32575 having an international filing date of Oct. 17, 2001 and published in English under PCT Article 21(2) and claims the benefit of provisional application Ser. No. 60/401,836, filed Aug. 6, 2002, the entire teachings of which are incorporated herein by reference.

FEDERALLY SPONSORED RESEARCH OR DEVELOPMENT

The U.S. Government may have certain rights in this invention pursuant to Grant Nos. NIDA RO1 DA11542, and NIDA NO1 DA7-8081, awarded by NIDA (NIH).

TECHNICAL FIELD

This invention relates to novel compositions with affinity for a monoamine transporter, such as the dopamine, norepinephrine, or serotonin transporter, in brain and in peripheral tissues.

BACKGROUND OF THE INVENTION

Monoamine transporters play a variety of roles, and compounds with affinity for the monoamine transporters have been proposed for therapy and/or diagnosis of medical indications that include (but are not limited to) attention deficit hyperactivity disorder (ADHD), Parkinson's disease, cocaine addiction, smoking cessation, weight reduction, obsessive-compulsive disorder, various forms of depression, traumatic brain injury, stroke, and narcolepsy.

The dopamine transporter (DAT) in particular is a primary mechanism for terminating the effects of synaptic dopamine and maintaining homeostatic levels of extracellular dopamine in brain. Giros et al., Nature 379: 606–612 (1996). The dopamine transporter is a principal target of therapeutic and psychostimulant drugs of abuse. For example, the dopamine transporter is an important target of drugs (including methylphenidate, pemoline, amphetamine and bupropion) used to treat ADHD. Seeman and Madras, Mol. Psychiatry 3:386–396 (1998); Cyr and Brown, Drugs, 56:215–223 (1998); Biederman, J. Clin. Psychiatry 59: 4–16 (1998); Riggs et al., J. Am Acad. Child Adolesc. Psychiatry 37:1271–1278 (1999). The dopamine transporter is also a principal target of brain imaging agents used, for example, diagnostically.

It has been suggested that the therapeutic benefit of benztropin (Cogentin®) for Parkinson's disease results in part from blocking dopamine transport thereby increasing synaptic dopamine. Coyle and Snyder, J. Pharmacol. Exp. Ther., 170:221–319 (1969).

The antidepressant bupropion apparently is also a monoamine transport inhibitor [Hirschfeld, J. Clin. Psychiatry 17: 32–35 (1999)], and it has been suggested as a treatment to aid smoking cessation. Jorenby et al., N. Engl. J. Med., 340:685–691 (1999); McAfee et al., N. Engl. J. Med., 338:619 (1998).

The dopamine transporter has been identified as an effective marker for dopamine terminals in Parkinson's disease. Kaufman and Madras, Synapse 9: 43–49 (1991). Brain imaging of the transporter in humans with Parkinson's disease and in animals with experimentally produced Parkinsonism has confirmed the usefulness of the dopamine transporter in this application. Fischman et al., Synapse 29: 128–141, 1998, Seibyl et al., Ann. Neurol. 38:589–598.

The serotonin transporter (SERT) regulates extracellular serotonin levels. It is a principal target of effective drugs (known as serotonin-selective reuptake inhibitors or SSRI's) used to treat melancholic depression, a typical depression, dysthymia and obsessive-compulsive disorder. It also is a conduit of entry into serotonin containing neurons of neurotoxic substituted amphetamines. Selective imaging agents that label the serotonin transporter would be useful to investigate the status of the transporter in depression [Malison et al. Bio. Psychiatry 44:1090–1098 (1998)], alcoholism [Heinz et al. Am. J. Psychiatry 155:1544–1549 (1998)], obsessive-compulsive disorder, and substituted amphetamine abusers [McCann et al., Lancet 352:1433–1437 (1998); Semple et al., Br., J. Psychiatry 175: 63-39 (1999)]. There are various reports generally dealing with individual serotonin transporter imaging agents. Acton et al. Eur. J. Nucl. Med. 26:1359–1362 (1999); Szabo et al. J. Cereb. Blood Flow Metab. 19:967–981 (1999); Oya et al. J. Med. Chem. 42:333–335 (1999).

Norepinephrine regulates mood, is involved in learning and memory, and controls endocrine and autonomic functions. Dysfunction of norepinephrine neurotransmission has been implicated in depression, cardiovascular and thermal pathophysiology. The norepinephrine transporter (NET) regulates extracellular levels of norepinephrine in brain, in heart, and in the sympathetic nervous system. Clinically, the norepinephrine transporter is a principal target of selective or non-selective anti-depressant drugs and stimulant drugs of abuse such as cocaine and amphetamines. Blockade of the norepinephrine transporter is implicated in appetite suppression. Gehlert et al. J. Pharmacol. Exp. Ther. 287:122–127 (1998). Imaging of the norepinephrine transporter may also be useful for viewing the status of sympathetic innervation in the heart and in other adrenergic terminals, and for detecting neuroblastomas. Hadrich et al. J. Med. Chem. 42:3010–3018 (1999); Raffel et al., J. Nucl. Med. 40:323–330 (1999).

It is desirable to avoid unwanted side effects of treatments targeting monoamine transporters, to the extent possible. It is also desirable to produce efficient and effective diagnostics for various conditions involving monoamine transporters.

SUMMARY OF THE INVENTION

The invention features compounds of two general classes that have high and selective monoamine transport affinity. Featured compounds of the first class (which we term oxaindanes) generally have the following formula:

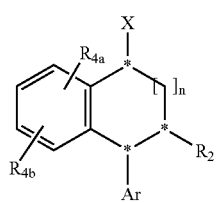

WHERE:
* indicates a chiral center, and each chiral center, independently, may be R, S, or R/S
—X=—CH$_2$R$_1$; —CHR$_1$R$_5$; —CR$_1$=O; —CR$_6$=O; —O—R$_1$; —SR$_1$; —SOR$_6$; —SO$_2$R$_6$; —SO$_2$NHR$_1$; or —CH=CR$_1$R$_5$ and where:
  a. —R$_1$ and —R$_5$ are independently selected from: —H; —CH$_3$; —CH$_2$CH$_3$; or —CH$_2$(CH$_2$)$_m$CH$_3$, where m=0, 1, 2, or 3;
     PROVIDED THAT, when X=—O—R$_1$, then R$_1$≠H; and
  b. —R$_6$ is selected from: —OH; —OCH$_3$; —NHR$_1$; —O-alkyl; —O-alkenyl; —O-alkynyl; —O-allyl; —O-iodoallyl; -alkyl; -alkenyl; -alkynyl; -allyl; -isopropyl; and -isobutyl;
—Ar=either
  a) phenyl substituted at any two positions with R$_{3a}$ and R$_{3b}$, where R$_{3a}$ and R$_{3b}$ are as defined in options "I." or "II.", below; or
  b) 1-napththyl or 2-naphthyl, substituted at any two positions with R$_{3a}$, and R$_{3b}$ where R$_{3a}$ and R$_{3b}$ are as defined in option "I.", below);
     OPTION I for R$_{3a}$, R$_{3b}$ (phenyl or naphthyl substitutions)
       —R$_{3a}$ and —R$_{3b}$ are independently selected from: —H; —Br; —Cl; —I; —F; —OH; —OCH$_3$; —CF$_3$; —NO$_2$; —NH$_2$; —CN; —NHCOCH$_3$, —C(CH$_3$)$_3$, —(CH$_2$)qCH$_3$ where q=0–6; —COCH$_3$; —F (at the 2, 3 or 4 position), —Cl (at the 2, 3 or 4 position); —I (at the 2, 3 or 4 position); alkyl; alkenyl; alkynyl; allyl; iospropyl; isobutyl; alkyl; -alkylN$_2$S$_2$ chelator; -alkylN$_2$S$_2$Tc chelator, such that N$_2$S$_2$ is part of a chelating moiety such as those known in the art which contain two nitrogens and two sulfur atoms, in addition to carbon and optionally other heteroatoms, see, for example, O'Neil et al., *Bioconjugate Chem.*, 5:182–193 (1994); O'Neil et al., *Inorgan. Chem.*, 33:319–323(1994); Kung et al., *J. Nucl. Med.* 27:1051 (1986); Kung et al., *J. Med. Chem.* 28:1280–1284 (1985), hereby incorporated by reference; or COR$_7$, where R$_7$ is defined below; or
     OPTION II. for R$_{3a}$, and R$_{3b}$ (phenyl substitutions)
       —R$_{3a}$ and —R$_{3b}$ as a pair are independently selected from the following pairs: 3,4-diCl; 3,4,diOH; 3,4-diOAc; 3,4-diOCH$_3$; 3-OH,4-Cl; 3-OH,4-F; 3-Cl,4-OH; or 3-F,4-OH;
n=0 or 1;
—R$_2$=H, —COOCH$_3$; —COR$_7$; -alkyl; -alkenyl; -allyl; -iodoallyl; -alkynyl; -isoxazole; -oxadiazole; -oxazole; -alkylN$_2$S$_2$ chelator-; —O-alkylN$_2$S$_2$ chelator; -alkylN$_2$S$_2$Tc chelator; —O-alkylN$_2$S$_2$Tc chelator; where, —R$_7$ is=—NHR$_8$; morpholinyl; piperidinyl; —CH$_3$; —CH$_2$CH$_3$; —CH$_2$(CH$_2$)$_r$CH$_3$ where r=0, 1, 2, or 3; alkyl; alkenyl; alkynyl; allyl; isopropyl; iodoallyl; O-iodoallyl; -isobutyl; —CH$_2$SO$_2$; -alkylN$_2$S$_2$ chelator; -alkylN$_2$S$_2$Tc chelator; O-alkylN$_2$S$_2$ chelator; or —O-alkylN$_2$S$_2$Tc chelator; and
—R$_8$ is=-alkyl; -alkenyl; -allyl; -iodoallyl; -alkynyl; -isoxazole; -oxadiazole; -oxazole; -alkylN$_2$S$_2$ chelator; —O-alkylN$_2$S$_2$ chelator; -alkylN$_2$S$_2$Tc chelator; or —O-alkylN$_2$S$_2$Tc chelator;
R4a and R4b are independently selected from: —H; —Br; —Cl; —I; —F; —OH; —OCH$_3$; —CF$_3$; —NO$_2$; —NH$_2$; —CN; —NHCOCH$_3$, C(CH$_3$)$_3$, —(CH$_2$)$_q$CH$_3$ where q=0–6; —COCH$_3$; —F (at the 2, 3 or 4 position), —Cl (at the 2, 3 or 4 position); —I (at the 2, 3 or 4 position); alkyl; alkenyl; alkynyl; allyl; iospropyl; isobutyl; alkyl; -alkylN$_2$S$_2$; -alkylN$_2$S$_2$Tc; and COR$_7$, where R$_7$ is defined above; or
R4a and R4b are selected as a pair from the following pairs: 3,4-diCl; 3,4-diOH; 3,4-diOAc; 3,4-diOCH$_3$; 3-OH,4-Cl; 3-OH,4-F; 3-Cl,4-OH; and 3-F,4-OH.

Preferred substituents for the above general formula are as follows: n is preferably 0; X is preferably —O—R$_1$, where R$_1$ is preferably —CH$_3$; Ar is preferably phenyl or napthyl (1- or 2-napththyl), substituted at any two positions with R$_{3a}$, and R$_{3b}$; e.g., R$_{3a}$ and R$_{3b}$ may independently be —Cl, —H. Particularly preferred compounds are O-1617; O-1630; O-1833; O-1925, described below in Table 2.

The second general class of compounds (which we generally term tetrahydropyranyl esters or THP esters) generally have one of the following three formulas:

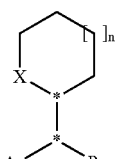

A

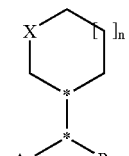

B

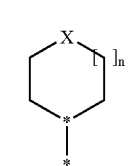

C

Where:
n is 0, 1, 2, or 3;
>X is >CH$_2$; >CHY; >C(Y,Z); >C=O; >O; >S; >SO; >SO$_2$; >NSO$_2$; >NSO$_2$R$_3$; or >C=CYZ;
  where Y and Z are independently selected from H; Br; Cl; I; F; OH; OCH$_3$; CF$_3$; NO$_2$; NH$_2$; CN; NHCOCH$_3$; N(CH$_3$)$_2$; (CH$_2$)$_m$CH$_3$, where m=0–6; COCH$_3$; alkyl alkenyl, alkynyl, allyl, isopropyl, isobutyl;
—Ar=either
  a) phenyl substituted at any two positions with R$_{1a}$ and R$_{1b}$, where R$_{1a}$ and R$_{1b}$ are as defined in options "I." or "II.", below; or
  b) 1-napththyl or 2-naphthyl, substituted at any two positions with R$_{1a}$ and R$_{1b}$ where R$_{1a}$ and R$_{1b}$ are as defined in option "I.", below);
OPTION I for R$_{1a}$, and R$_{1b}$ (phenyl or naphthyl substitutions)
  —R$_{1a}$ and —R$_{1b}$ are independently selected from: —H; —Br; —Cl; —I; —F; —OH; —OCH$_3$; —CF$_3$; —NO$_2$; —NH$_2$; —CN; —NHCOCH$_3$, —C(CH$_3$)$_3$, —(CH$_2$) qCH$_3$ where q=0–6; —COCH$_3$; —F (at the 2, 3 or 4 position), —Cl (at the 2, 3 or 4 position); —I (at the 2, 3 or 4 position); alkyl; alkenyl; alkynyl; allyl; iospropyl; isobutyl; alkyl; -alkylN$_2$S$_2$ chelator; -alkylN$_2$S$_2$Tc chelator; or COR$_4$, where R$_4$ is defined below; or OPTION II. for $R_{1a}$ and $R_{1b}$ (phenyl substitutions)

- —$R_{1a}$ and —$R_{1b}$ as a pair are independently selected from the following pairs: 3,4-diCl; 3,4,diOH; 3,4-diOAc; 3,4-diOCH$_3$; 3-OH,4-Cl; 3-OH,4-F; 3-Cl,4-OH; or 3-F, 4-OH;
- —$R_2$=—COOCH$_3$; —COR$_4$; -alkyl; -alkenyl; -allyl; -iodoallyl; -alkynyl; -isoxazole; -oxadiazole; -oxazole; -alkylN$_2$S$_2$ chelator; —O-alkylN$_2$S$_2$ chelator; -alkylN$_2$S$_2$Tc chelator; —O-alkylN$_2$S$_2$Tc chelator; or

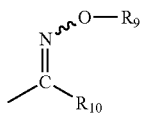

where,
- —$R_4$ is=—NHR$_5$; morpholinyl; piperidinyl; —CH$_3$; —CH$_2$CH$_3$; —CH$_2$(CH$_2$)$_r$CH$_3$ where r=0, 1, 2, or 3; alkyl; alkenyl; alkynyl; allyl; isopropyl; iodoallyl; O-iodoallyl; -isobutyl; —CH$_2$SO$_2$; -alkylN$_2$S$_2$ chelator; -alkylN$_2$S$_2$Tc chelator; O-alkylN$_2$S$_2$ chelator; or —O-alkylN$_2$S$_2$Tc chelator; and
- —$R_5$ is=-alkyl; -alkenyl; -allyl; -iodoallyl; -alkynyl; -isoxazole; -oxadiazole; -oxazole; -alkylN$_2$S$_2$ chelator; —O-alkylN$_2$S$_2$ chelator; -alkylN$_2$S$_2$Tc chelator; —O-alkylN$_2$S$_2$Tc chelator, and
- $R_9$ and $R_{10}$ are independently=H, CH$_3$, CH$_2$CH$_3$, (CH$_2$)$_r$CH$_3$, (CH$_2$)$_r$C$_6$H$_3$YZ, isopropyl isobutyl, CH=CH—(CH$_2$)$_r$CH$_3$, CH$_2$CH=CH(CH$_2$)$_r$CH$_3$, (CH$_2$)$_s$CH=CH(CH$_2$)$_r$CH$_3$, C C(CH$_2$)$_r$CH$_3$, CH$_2$ C C(CH$_2$)$_r$CH$_3$, where r=0–6 and s=0–6 and Y and Z are independently=H, F, Cl, Br, I, OH, OR, CH$_3$, CF$_3$, amino, NO$_2$.

In one preferred compounds are those with the following substituents: X is preferably O; n is preferably 1; preferably the compound has formula A, above; $R_2$ is preferably —COR$_4$, most preferably —COOCH$_3$; —Ar is preferably phenyl substituted at any two positions with $R_{3a}$, and $R_{3b}$, e.g., where $R_{3a}$, and $R_{3b}$ are independently selected from —H and —Cl. $R_4$ is —OCH$_3$ or —C$_2$H$_5$. Particularly preferred compounds are compounds: 1a (compound O-1793), 1b (compound O-1792), 2a (compound O-1794), 2b (compound O-1783), and the corresponding carboxylic acids, 3a, 3b, 4a, or 4b.

In another embodiment, X is preferably C; n is preferably 1; preferably the compound has formula A, above; $R_2$ is —COOCH$_3$; —Ar is preferably phenyl substituted at any two positions with $R_{3a}$, and $R_{3b}$, e.g., where $R_{3a}$, and $R_{3b}$ are independently selected from —H and —Cl. Examples of preferred compounds include α-cyclohexyl-3,4-dichlorobenzylcyanide and α-cyclohexyl-3,4-dichlorophenylcyclohexyl acetic acid methyl ester.

In another embodiment, X is preferably C; n is preferably 0 (the ring is a cyclopentyl group); preferably the compound has formula A, above; $R_2$ is preferably —COOCH$_3$; —Ar is preferably phenyl substituted at any two positions with $R_{3a}$, and $R_{3b}$, e.g., where $R_{3a}$, and $R_{3b}$ are independently selected from —H and —Cl. Examples of preferred compounds include α-cyclopentyl-3,4-dichlorobenzylcyanide and α-cyclopentyl-3,4-dichlorophenylcyclohexyl acetic acid methyl ester, compounds 10 and 11, respectively.

As noted above, other embodiments include compounds in which $R_2$ is an imine function such as:

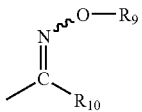

This function is synthesized from the corresponding ketone by standard techniques using the appropriate amine. The resulting imines show increased bioavailability and surprising stability under the temperature and pH conditions of the stomach. See, Palani et al., *J. Med. Chem.* 44:3339 (2001).

Compounds of the above formula which demonstrate monoamine transport affinity are useful for labeling receptor-expressing cells using in vitro techniques that are generally known to those skilled in the field and are generally described below. They may also be used for in vivo imaging in the conditions described above and to treat various medical indications, including attention deficit hyperactivity disorder (ADHD), Parkinson's disease, cocaine addiction, smoking cessation, weight reduction, obsessive-compulsive disorder, various forms of depression, traumatic brain injury, stroke, and narcolepsy. A more exhausive list of medical indications where the compounds have diagnostic or therapeutic utility includes: depression and related disorders, seasonal affective disorders, sexual dysfunction, sexual behavior disorders, attention deficit hyperactivity disorder, learning deficit, senile dementia, disorders involving the release of acetylcholine, including memory deficits, dementia of aging, AIDS-dementia, senile dementia, pseudodementia, presenile dementia), autism, mutism, cognitive disorders, dyslexia, tardive dyskinesia, hyperkinesia, anxiety, panic disorders, paranoia, obsessive-compulsive disorder, post-traumatic syndrome, social phobia, other phobias, psychosis, bipolar disorder and other psychiatric or clinical disfunctions, mania, manic depression, schizophrenia (deficient form and productive form) and acute or chronic extrapyramidal symptoms induced by neuroleptic agents, obsessive compulsive disorders (OCD), chronic fatigue syndrome, for enhancing alertness, attention, arousal and vigilance, narcolepsy, disorders of sleep, jet-lag, obesity, bulimic and other eating disorders, anorexia nervosa, cocaine and other drug addiction or misuse, alcoholism, tobacco abuse, neurological disorders including epilepsy, traumatic brain injury, treatment of neurodegenerative diseases, including Parkinson's Disease, Alzheimer's Disease, Huntington's Disease, Amyotrophic Lateral Sclerosis, Gilles de la Tourette's syndrome, the treatment of mild, moderate or even severe pain of acute, chronic or recurrent character, as well as pain caused by migraine, postoperative pain, and phantom limb pain, disorders linked to decreased transmission of serotonin in mammals, including Ganser's syndrome, migraine headache, pre-menstrual syndrome or late luteal phase syndrome, and peripheral neuropathy.

The invention also includes methods of making medicaments for treating the above indications, as well as pharmaceutical compositions comprising the compounds formulated to treat those indications, e.g., with a pharmaceutically acceptable carrier.

The invention also includes method of using the above compounds diagnostically or in research (e.g., using scanning techniques such as PET or DAT) to determine physiological conditions associated with altered function distribution number or density of dopamine norepinephrine or serotonin transporters which lead to behavioral and neuordegenerative disorders or diseases such as those listed above. In that case the compounds typically will be labeled by substituting an atom with one of its corresponding radioisotope (e.g., substitute H with $^3$H, or F with $^{18}$F). Alternatively, the compounds a radioactive substituent may be added to the compound.

The details of one or more embodiments of the invention are set forth in the accompanying structures and the description below. Other features, objects, and advantages of the invention will be apparent from the following description and structures, and from the claims.

DETAILED DESCRIPTION OF THE FIGURES

DETAILED DESCRIPTION

Figure 1:
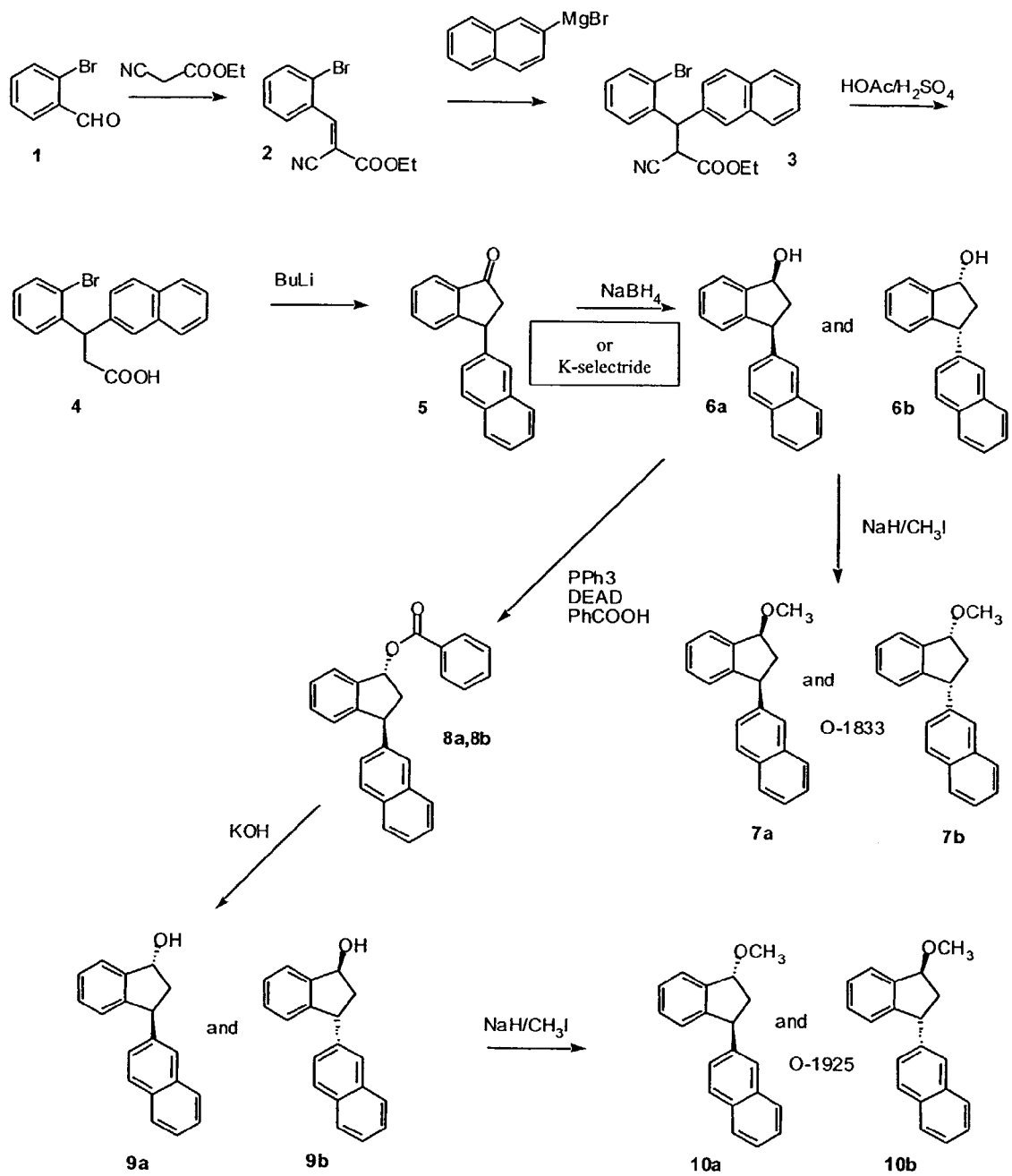
FIG. 1 shows the synthesis of 3-aryl substituted oxaindanes.

The compounds according to the invention are detailed above and in the claims. Formulation into pharmaceuticals, and use of those pharmaceuticals are detailed below. In therapeutic applications, the compound may be administered with a physiologically acceptable carrier, such as physiological saline. The therapeutic compositions of the invention can also contain a carrier or excipient, many of which are known to skilled artisans. Excipients that can be used include buffers (e.g., citrate buffer, phosphate buffer, acetate buffer, and bicarbonate buffer), amino acids, urea, alcohols, ascorbic acid, phospholipids, proteins (e.g., serum albumin), EDTA, sodium chloride, liposomes, mannitol, sorbitol, and glycerol. The compounds of the invention can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences."

Routes of administration are also well known to skilled pharmacologists and physicians and include intraperitoneal, intramuscular, subcutaneous, rectal and intravenous administration. Additional routes include intracranial (e.g., intracisternal or intraventricular), intraorbital, opthalmic, intracapsular, intraspinal, intraperitoneal, transmucosal, topical, subcutaneous, and oral administration. It is expected that the oral route will be preferred for the administration of the compounds. The subcutaneous route may also be used. Another route of administration of the compounds that is feasible is the intraperitoneal route. Systemic administration of the compounds can also be effective. Thus, while one may target the compounds more specifically to their site of action, such targeting is not necessary for effective treatment.

It is well known in the medical arts that dosages for any one patient depend on many factors, including the general health, sex, weight, body surface area, and age of the patient, as well as the particular compound to be administered, the time and route of administration, and other drugs being administered concurrently. Dosages for the compound of the invention will vary, but can, when administered intravenously, be given in doses of approximately 0.01 mg to 100 mg/ml blood volume. A dosage can be administered one or more times per day, if necessary, and treatment can be continued for prolonged periods of time, up to and including the lifetime of the patient being treated. If a compound of the invention is administered subcutaneously, the dosage can be reduced, and/or the compound can be administered less frequently. Determination of correct dosage for a given application is well within the abilities of one of ordinary skill in the art of pharmacology. In addition, those of ordinary skill in the art can turn to data and experiments presented below for guidance in evaluating the binding properties of compounds, e.g., when developing an effective treatment regime. Additionally, one could begin tailoring the dosage of the compounds required for effective treatment of humans from the dosage proven effective in the treatment of small mammals. Routine experimentation would be required to more precisely define the effective limits of any given administrative regime. For example, in a conservative approach, one could define the lowest effective dosage in small mammals, and administer that dose to progressively larger mammals before beginning human safety trials.

This invention will be illustrated further by the following examples. These examples are not intended to limit the scope of the claimed invention in any manner. The Examples provide suitable methods for preparing compounds of the present invention. However, those skilled in the art may make compounds of the present invention by any other suitable means. As is well known to those skilled in the art, other substituents can be provided for the illustrated compounds by suitable modification of the reactants.

I. Synthesis of Oxaindanes

The following general description relates to the synthesis of the oxaindane analogs.

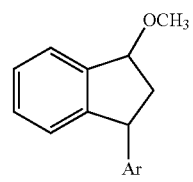

Cis- and Trans-1-methoxy-3-aryl-indans

The general synthesis of the 3-aryl substituted oxaindanes was accomplished via the route presented in the scheme for the 3-naphthyl analogs shown below. The synthesis of the four isomers (two diastereomers 7 and 10, and a pair of enantiomers of each, a and b), was accomplished via an intermediate described by Bøgesø, K. P. et al., *J. Med. Chem.* 28, 1817–1828 (1985). Thus, the cis diastereomers 6a and 6b were prepared in five steps from 2-bromobenzaldehyde. These cis alcohols 6a and 6b were then methylated with sodium hydride and methyl iodide to provide the target cis-methoxyindans 7a and 7b. Inversion of stereochemistry at the C-1 position was accomplished via Mitsunobu inversion by reaction with benzoic acid in the presence of triphenyl phosphine and diethylazodicarboxylate to provide the trans enantiomers 8a and 8b (only one enantiomer is shown in the scheme in FIG. 1). Methylations, as for alcohols 6a and 6b, then provided the target trans-methoxyindans 10a and 10b.

Experimental Section

Experimental details for the above general synthesis follow.

NMR spectra were recorded in CDCl$_3$ on a JEOL 300 NMR spectrometer operating at 300.53 MHz for $^1$H, and 75.58 MHz for $^{13}$C. TMS was used as internal standard. Melting points are uncorrected and were measured on a Gallenkamp melting point apparatus. Thin layer chromatography (TLC) was carried out on Baker Si250F plates. Visualization was accomplished with either UV exposure or treatment with phosphomolybdic acid (PMA). Flash chromatography was carried out on Baker Silica Gel 40 mM. Elemental analyses were performed by Atlantic Microlab, Atlanta, Ga. All reactions were conducted under an inert (N$_2$) atmosphere.

Ethyl 2-cyano-3-(2-bromophenyl)-2-propenoate, 2.

2-Bromobenzaldehyde 1 (10.0 g, 54.0 mmol), ethyl cyanoacetate (6.91 g, 61.1 mmol) and piperidine (0.11 mL, 1.08 mmol) in toluene (45 mL) were refluxed at 135° C. with a Dean-Stark trap for 3 h. The solvent was removed on a rotary evaporator. The residue was crystallized from isopropyl ether to give 2 as a white powder (12.0 g, 75%): R$_f$ 0.3 (10% EtOAc/hexanes); $^1$H-NMR (CDCl$_3$) δ 8.63 (s, 1H), 8.17 (dd, 1H, J=8, 2 Hz), 7.70 (dd, 1H, J=8, 1 Hz), 7.35–7.49 (m, 2H), 4.32 (q, 2H, J=7 Hz), 1.41 (t, 3H, J=7 Hz).

Ethyl 3-(2-bromophenyl)-3-(2-naphthyl)-2-cyanopropanoate, 3.

Magnesium (90 mg, 3.66 mmol) was added into a solution of 2-bromonaphthalene (0.76 g, 3.66 mmol) and dibromoethane (37 TL, 0.43 mmol) in THF (15 mL). The reaction was stirred at room temperature for 30 min, and 1 h at 70° C. The reaction was then cooled to room temperature, followed by the addition of ethyl 2-cyano-3-(2-bromophenyl)-2-propenoate, 2 (1.00 g, 3.05 mmol). The reaction mixture was then refluxed at 70° C. overnight. 3N HCl (3 mL) and H$_2$O (5 mL) were added dropwise. The water layer was extracted with ether (3×30 mL). The organic solvent was removed on a rotary evaporator. The residue was purified by flash chromatography (20% EtOAc/hexanes) to afford 0.87 g (63%) of 3 as a colorless oil: R$_f$ 0.46 (10% EtOAc/hexanes); $^1$H-NMR (CDCl$_3$) δ 7.72–7.96 (m, 4H), 7.63 (td, 1H, J=9, 1 Hz) 7.24–7.52 (m, 5H), 7.1–7.2 (m, 1H), 5.45–5.49 (m, 1H), 4.40 (dd, 1H, J=12, 8 Hz), 4.01–4.21 (m, 2H), 1.08 (dt, 3H, J=22, 7 Hz).

3-(2-Bromophenyl)-3-(2-naphthyl)propanoic Acid, 4.

Ethyl 3-(2-bromophenyl)-3-(2-naphthyl)-2-cyanopropanoate, 3 (0.84 g, 1.84 mmol), glacial acetic acid (10 mL), conc. H$_2$SO$_4$ (5 mL), and H$_2$O (5 mL) were refluxed at 100° C. for 24 h. The reaction mixture was poured into ice and extracted with EtOAc (2×40 mL). The organic solvent was removed on a rotary evaporator. The crude solid was stirred in 3M KOH (5 mL) for 30 min. The basic aqueous solution was extracted with CHCl$_3$ (3×10 mL). The basic aqueous solution was acidified with 3N HCl to pH 4. The acidic solution was then extracted with EtOAc (3×20 mL). The organic solvent was removed on a rotary evaporator to give 4 (0.47 g, 72%) as a white solid: R$_f$ 0.4 (40% EtOAc/hexanes); $^1$H-NMR (CDCl$_3$) δ 7.69–7.79 (m, 4H), 7.54 (dd, 1H, J=8, 1 Hz), 7.40–7.48 (m, 2H), 7.33 (dd, 1H, J=9, 2 Hz), 7.17–7.25 (m, 2H), 7.02–7.08 (m, 1H), 5.18 (t, 1H, J=8 Hz), 3.13 (d, 2H, J=8 Hz).

3-(2-Naphthyl)indanone. 5.

n-BuLi (2.5 M in hexane, 1.2 mL, 2.91 mmol) was added dropwise into a solution of 3-(2-bromophenyl)-3-(2-naphthyl) propanoic acid, 4 (0.47 g, 1.32 mmol) at –10° C. The reaction mixture was stirred at 0° C. in an ice bath for 4 h. 3N HCl (2 mL) and H$_2$O (3 mL) were added. The H$_2$O layer was extracted with ether (3×20 mL). The organic solvent was removed on a rotary evaporator. The residue was purified by flash chromatography (20% EtOAc/hexanes) to afford 5 (155 mg, 45%) as a colorless oil: R$_f$ 0.46 (10% EtOAc/hexanes); $^1$H-NMR (CDCl$_3$) δ 7.84 (d, 1H, J=8 Hz), 7.71–7.77 (m, 3H), 7.62 (d, 1H, J=1 Hz), 7.36–7.52 (m, 4H), 7.22 (dd, 1H, J=8, 1 Hz), 7.08 (dd, 1H, J=8, 2 Hz), 4.66 (q, 1H, J=4 Hz), 3.23 (dd, 1H, J=19, 8 Hz), 2.74 (dd, 1H, J=19, 4 Hz).

Cis-3-(2-Naphthyl)indan-1-ol, 6a and 6b.

K-Selectride (1M in THF, 1.20 mL, 1.20 mmol) was added into a solution of 3-(2-naphthyl)indanone, 5 (155 mg, 0.60 mmol) at 0° C. The reaction was stirred at 0° C. for 4 h. H$_2$O (5 mL) was added and the reaction mixture was extracted with ether (3×20 mL). Ether was removed on a rotary evaporator. $^1$H-NMR of the crude residue confirmed the structure. The crude residue was used for next step without further purification.

Cis-3-(2-Naphthyl)-0-methylindanol, 7a and 7b.

Sodium hydride (60% dispersion, 80 mg, 2.15 mmol) was added into a solution of cis-3-(2-naphthyl)-indan-1-ol 6a and 6b (140 mg, 0.538 mmol) and methyl iodide (0.13 mL, 2.15 mmol) in THF (3 mL). The reaction mixture was stirred overnight. H$_2$O (4 mL) was added and the reaction mixture was extracted with ether (3×20 mL). The organic solvent was removed on a rotary evaporator. The residue was purified by flash chromatography (10% EtOAc/hexanes) to afford 0.10 g (68%) of 7a and 7b as a colorless oil: R$_f$ 0.57 (10% EtOAc/hexanes); $^1$H-NMR (CDCl$_3$) δ 7.75–7.80 (m, 3H), 7.71 (s, 1H), 7.38–7.58 (m, 3H), 7.25–7.32 (m, 2H), 7.20 (td, 1H, J=7, 1 Hz), 6.93 (d, 1H, J=7 Hz), 4.95 (t, 1H, J=7 Hz), 4.34 (t, 1H, J=8 Hz), 3.51 (s, 3H), 2.99 (qd, 1H, J=7, 6 Hz), 2.09 (qd, 1H, J=7, 6 Hz).

Trans-Benzoic acid 3-(2-naphthyl)indan-1-yl esters, 8a and 8b.

Triphenylphosphine (1.44 g, 5.49 mmol) and benzoic acid (0.60 g, 4.91 mmol) were added to a solution of cis-3-(2-naphthyl)-indan-1-ol, 6a and 6b (0.645 g, 2.48 mmol) in anhydrous THF (20 mL). The reaction was treated dropwise with a solution of DEAD in THF (4.95 M, 1 mL) then stirred under nitrogen atmosphere at room temperature. After 3 h, the reaction solution was directly filtered through a pad of silica and condensed. The resulting residue was purified by radial chromatography (4 mm plate, 10% ethyl acetate/hexanes) yielding a mixture of enantiomers 8a and 8b as an off-white solid (0.72 g, 80%): R$_f$=0.46 in 10% ethyl acetate/hexanes; $^1$H-NMR (CDCl$_3$) δ 8.08–8.05 (m, 2H), 7.84–7.78 (m, 3H), 7.71 (bs, 1H), 7.58–7.41 (m, 4H), 7.35–7.29 (m, 2H), 7.24 (dd, 2H, J=5.7, 2.7), 7.07–7.04 (m, 1H), 6.62 (dd, 1H, J=6.3, 1.9), 4.88 (t, 1H, J=7.7), 2.83 (ddd, 1H, J=2.2, 7.7, 14.6), 2.69–2.60 (ddd, 1H, J=6.6, 7.98, 14.6).

Trans-3-(2-Naphthyl)indan-1-ol, 9a and 9b.

Trans-3-(2-Naphthyl)indan-1-benzoate esters, 8a and 8b (0.681 g, 1.87 mmol) were dissolved in THF (60 mL) and methanol (35 mL) was added. Aqueous potassium hydroxide (3M, 10 mL) was added and the reaction solution was stirred vigorously at room temperature for 1.5 h until no starting material was detected by TLC. The methanol was removed in vacuo and the remaining solution was acidified to pH=3 with 3 M HCl (aq). The aqueous solution was extracted with ether (3×50 mL) and the combined organic layers were concentrated in vacuo. The residue was purified by radial chromatography (4 mm plate, 30% ethyl acetate/hexanes) to provide the enantiomers 9a and 9b as a clear oil (0.347 g, 71%) which foamed under high vacuum: R$_f$=0.37 in 30% ethyl acetate/hexanes; $^1$H-NMR (CDCl$_3$) δ 7.89–7.73 (m, 3H), 7.59 (bs, 1H), 7.50–7.41 (m, 3H), 7.32–7.15 (m, 3H), 5.40 (dd, 1H, J=3.0, 6.3), 4.77 (t, 1H, J=7.4), 2.58 (ddd, 1H, J=2.8, 7.7, 13.8), 2.45 (ddd, 1H, J=6.3, 7.2, 13.8), 2.14 (bs, 1H).

Trans-1-Methoxy-3-(2-naphthyl)indans, 10a and 10b.

Sodium hydride (64.0 mg, 1.60 mmol) and methyl iodide (95.0 µL, 1.53 mmol) were added to a solution of trans-3-(2-naphthyl)indan-1-ols 9a and 9b (0.100 g, 0.384 mmol) at room temperature. The reaction was stirred under a nitrogen atmosphere for 16 h. The reaction was quenched with excess water (25 mL), then extracted with ether (3×25 mL). The combined ethereal phases were condensed to provide a yellow oil that solidified under vacuum. The crude solid was purified by flash chromatography (12 g silica, 10% ethyl acetate/hexanes) to afford the enantiomers 10a and 10b as a pale yellow oil (82 mg, 78%): $R_f$=0.47 in 10% ethyl acetate/hexanes; $^1$H-NMR (CDCl$_3$) δ 7.80–7.74 (m, 3H), 7.65 (bs, 1H), 7.51–7.41 (m, 3H), 7.30–7.17 (m, 3H), 7.01–6.98 (m, 1H), 4.92 (dd, 1H, J=1.7, 5.8), 4.76 (t, 1H, J=8.0), 3.43 (s, 3H), 2.70 (ddd, 1H, J=1.4, 7.43, 13.76), 2.34 (ddd, 1H, J=6.05, 7.7, 13.76). Anal. ($C_{20}H_{18}O$) C, H.

Ethyl 3-(2-bromophenyl)-3-(3,4-dichlorophenyl)-2-cyanopropanoate, (3: 3,4-Cl$_2$Ph).

Magnesium (0.30 g, 12.3 mmol) was added into a solution of 1,2-dichloro-4-bromobenzene (2.76 g, 12.2 mmol) in ether (6 mL) and the reaction was stirred for 3 h. A solution of ethyl 2-cyano-3-(2-bromophenyl)-2-propenoate (3 g, 9.15 mmol) in toluene (6 mL) was added into the reaction mixture via an addition funnel over 15 min. The reaction mixture was then heated to 90° C. and stirred for 45 min. Ether was collected by Dean-Stark trap. The reaction mixture was poured into ice containing conc. H$_2$SO$_4$ (1 mL). The H$_2$O layer was extracted with ether (3×40 mL). Ether was removed on a rotary evaporator affording the crude product as a yellow oil (4.49 g, quantitative): $R_f$ 0.32 (10% EtOAc/hexanes); $^1$H-NMR (CDCl$_3$) δ 7.57–7.63 (m, 7H), 5.24 (dd, 1H, J=8, 8 Hz), 4.11–4.29 (m, 3H), 1.16 (ddd, 3H, J=7, 7, 14 Hz).

3-(2-Bromophenyl)-3-(3,4-dichlorophenyl)-propanoic acid, (4: 3,4-Cl$_2$Ph).

Ethyl 3-(2-bromophenyl)-3-(3,4-dichlorophenyl)-2-cyanopropanoate (4.49 g, 9.45 mmol) in glacial acetic acid (20 mL), conc. H$_2$SO$_4$ (10 mL) and H$_2$O (10 mL) was refluxed at 100° C. for 24 h. The hot solution was poured into ice in a beaker. White powder was formed and extracted with EtOAc (3×50 mL). Removal of solvent afforded 3.2 g of an oily solid. The residue was stirred in 3N NaOH (20 mL) for 30 min. The H$_2$O layer was extracted with CHCl$_3$ (3×30 mL) to remove any organic side-products. The H$_2$O layer was then acidified to pH 5 with 3N HCl (10 mL). White solid precipitate was formed and collected by filtration through a sintered funnel. After drying in vacuo, the solid weighed 2.1 g (59%): $^1$H-NMR (CDCl$_3$) δ 7.56 (dd, 1H, J=8, 1 Hz), 7.27–7.37 (m, 3H), 7.08–7.19 (m, 3H), 4.96 (t, 1H, J=8 Hz), 2.95–3.11 (m, 2H).

3-(3,4-Dichlorophenyl)indanone, (5: 3,4-Cl$_2$Ph).

n-BuLi (2.5 M in hexanes, 4.15 mL, 10.4 mmol) was added dropwise over 15 min into a solution of ethyl 3-(2-bromophenyl)-3-(3,4-dichlorophenyl)-propanoic acid (1.77 g, 4.73 mmol) in ether (23 mL) at −10° C. After the addition, the reaction was allowed to stir at 0° C. in an ice bath for 40 min. 3N HCl (3 mL) was added slowly followed by H$_2$O (5 mL). The H$_2$O layer was extracted with ether (3×30 mL). The solvent was removed on a rotary evaporator. The residue was purified by flash chromatography (20% EtOAc/hexanes) to give a white solid (0.6 g, 46%): mp 112–113° C.; $R_f$ 0.39 (20% EtOAc/hexanes); $^1$H-NMR (CDCl$_3$) δ 7.82 (d, 1H, J=8 Hz), 7.60 (ddd, 1H, J=8, 8, 1 Hz), 7.42–7.48 (m, 1H), 7.37 (d, 1H, J=8 Hz), 7.24–7.27 (m, 1H), 7.22 (d, 1H, J=2 Hz), 6.94 (dd, 1H, J=8, 2 Hz), 4.54 (q, 1H, J=4 Hz), 3.23 (dd, 1H, J=19, 8 Hz), 2.61 (dd, 1H, J=19, 4 Hz). Anal. ($C_{15}H_{10}Cl_2O$) C, H, Cl.

Cis-3-(3,4-Dichlorophenyl)indan-1-ol, (6: 3,4-Cl$_2$Ph).

K-Selectride (1M in THF, 2.7 mL) was added dropwise into a solution of 3-(3,4-dichlorophenyl)indanone (0.36 g, 1.28 mmol) at 0° C. The reaction was allowed to stir at 0° C. for 3 h. 3M NaOH (0.5 mL) was added slowly followed by the addition of 30% H$_2$O$_2$ (0.5 mL). Water (20 mL) was added and the water layer was extracted with ether (3×20 mL). Ether was removed on a rotary evaporator. The residue was purified by flash chromatography to give 0.32 g (88%) of 6 as a colorless oil: $R_f$ 0.43 (EtOAc/hexanes); $^1$H-NMR (CDCl$_3$) δ 7.48 (d, 1H, J=7 Hz), 7.38 (d, 1H, J=8 Hz), 7.32–7.35 (m, 1H), 7.29–7.30 (m, 1H), 7.24–7.26 (m, 1H), 7.07 (dd, 1H, J=8, 2 Hz), 6.94 (d, 1H, J=8 Hz), 5.29 (q, 1H, J=7 Hz), 4.15 (t, 1H, J=8 Hz), 3.01 (qd, 1H, J=7, 8 Hz), 2.06 (d, 1H, J=7 Hz), 1.88 (qd, 1H, J=7, 9 Hz). Anal. ($C_{15}H_{12}OCl_2$) C, H, Cl.

Cis-1-Methoxy-3-(3,4-dichlorophenyl)indans, (7: 3,4-C$_{12}$Ph).

Sodium hydride (60% dispersion, 10 mg, 0.251 mol) was added into a solution of methyl iodide (16 mg, 0.25 mmol) and cis-3-(3,4-dichlorophenyl)indan-1-ol (35 mg, 0.125 mmol) in THF (1 mL). The mixture was stirred for 4 h. 3N HCl (1 mL) and H$_2$O (5 mL) were added and the water layer was extracted with ether (3×10 mL). Ether was removed on a rotary evaporator. The residue was purified by flash chromatography (10% EtOAc/hexanes) to afford 18 mg (49%) of 7 as a colorless oil: $R_f$ 0.71 (20% EtOAc/hexanes); $^1$H-NMR (CDCl$_3$) δ 7.46–7.49 (m, 1H), 7.23–7.38 (m, 4H), 7.07 (dd, 1H, J=8, 2 Hz), 6.93–6.96 (m, 1H), 4.90 (t, 1H, J=6 Hz), 4.17 (t, 1H, J=8 Hz), 2.94 (qd, 1H, J=7, 6 Hz), 1.96 (qd, 1H, J=7, 6 Hz). Anal. ($C_{16}H_{14}OCl_2$) C, H.

Benzoic acid 3-phenylindan-1-yl ester, (8: 3,4-Cl$_2$Ph).

Cis-3-(3,4-Dichlorophenyl)indan-1-ol (50 mg, 0.18 mmol), triphenylphosphine (0.100 g, 0.376 mmol), diethyl azodicarboxylate (0.06 mL, 0.358 mmol) and benzoic acid (44 mg, 0.358 mmol) in THF were stirred overnight. The organic solvent was removed on a rotary evaporator. The residue was purified by flash chromatography (10% EtOAc/hexanes) to afford 50 mg (73%) of 8 as a colorless oil: $R_f$ 0.63 (20% EtOAc/hexanes); $^1$H-NMR (CDCl$_3$) δ 8.02–8.05 (m, 2H), 7.51–7.63 (m, 2H), 7.25–7.47 (m, 6H), 7.00–7.05 (m, 1H), 6.55 (dd, 1H, J=6, 2 Hz), 4.66 (t, 1H, J=8 Hz), 2.78 (qd, 1H, J=7, 2 Hz), 2.47 (qd, 1H, J=7, 7 Hz).

Trans-3-(3,4-Dichlorophenyl)indan-1-ol, (9: 3,4-Cl$_2$Ph).

Potassium hydroxide (3M, 1 mL) was added into a solution of benzoic acid 3-phenyl-indan-1-yl ester (50 mg, 0.131 mmol) in methanol (2 mL) and THF (2 mL). The reaction mixture was stirred for 2 h. 3M HCl (0.5 mL) was added dropwise until pH=3.0, followed by the addition of H$_2$O (5 mL). The H$_2$O layer was extracted with ether (3×20 mL) to afford an oil (47 mg) $R_f$ 0.63 (20% EtOAc/hexanes). The crude oil was used in the next step without further purification.

Trans-1-Methoxy-3-(3,4-dichlorophenyl)indans, (10:3,4-Cl$_2$Ph).

Sodium hydride (60% dispersion, 26 mg, 0.674 mmol) was added into a solution of trans-3-(3,4-dichlorophenyl)indan-1-ol (47 mg, 0.168 mmol) and CH$_3$I (42 L, 0.674 mmol) in THF (2 mL). The reaction mixture was stirred overnight. H$_2$O (5 mL) was added and the H$_2$O layer was extracted with ether (3×20 mL). The organic solvent was removed on a rotary evaporator. The residue was purified by flash chromatography (10% EtOAc/hexanes) to afford 20 mg (50%) of a colorless oil: R$_f$ 0.50 (10% EtOAc/hexanes); $^1$H-NMR (CDCl$_3$) δ 7.44–7.48 (m, 1H), 7.36 (d, 1H, J=8 Hz), 7.25–7.32 (m, 2H), 7.23 (d, 1H, J=2 Hz), 6.96–7.00 (m, 2H), 4.87 (dd, 1H, J=6, 2 Hz), 4.55 (t, 1H, J=8 Hz), 3.41 (s, 3H), 2.65 (td, 1H, J=7, 2 Hz), 2.18 (qd, 1H, J=7, 8 Hz). Anal. (C$_{16}$H$_{14}$OCl$_2$) C, H, Cl.

II. Synthesis of Tetrahydropyranyl Esters

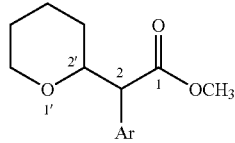

2-Aryl Tetrahydropyan-2-yl Acetic Acid Methyl Esters (Four Enantiomers)

In general, synthesis of the 2-aryl substituted tetrahydropyran-2-yl acetic acid methyl esters can be accomplished via an identical route to that presented below for the 2-(3,4-dichlorophenyl) analogs.

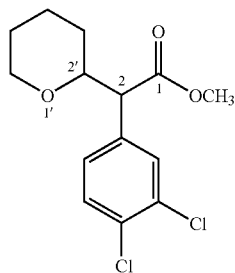

2-Chlorotetrahyropyran, prepared by passing hydrogen chloride gas into a solution of 2,3-dihydrotetrahydropyran in ether [Ficini, *J. Bull. Soc. Chim. Fr.* 119–124 (1956)], was reacted with the enolate of the appropriate methyl arylacetates to provide the desired product, exemplified below as a mixture of 1 and 2, in 77% yield (see Scheme 1 in FIG. 2).

Figure 3:
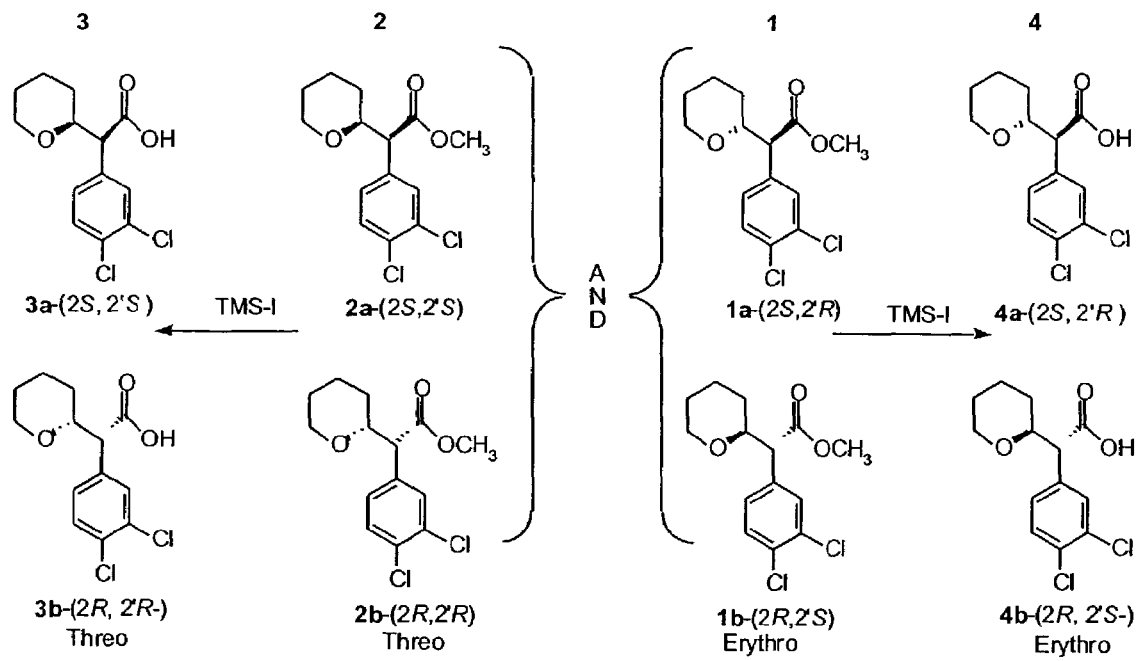
FIG. 3 shows synthesis of threo- and erythro-3,4-dicholorophenyltetrahydropyran-2-yl acetic acid (Scheme 2).

The product possesses two chiral centers (2, 2') and consequently there is a pair of enantiomers for each diastereomer. Therefore there exist four isomers as shown in Scheme 2 in FIG. 3 (Compounds 1 and 2).

The product mixture (1 and 2) obtained from the reaction of 2-chlorotetrahyropyran with the enolate of methyl 3,4-dichlorophenylacetate presented as two spots on TLC in a ratio of 1.0:1.4 ($^1$H-NMR). These two spots represent the two diastereomeric pairs of enantiomers 1 (1a and 1b) and 2 (2a and 2b).

The two diastereomers 1 and 2 were separated by column chromatography to obtain diastereomer 1 as an oil (2S,2'R and 2R,2'S) and diastereomer 2 as a solid (2S,2'S and 2R,2'R). (The assignment of chirality was achieved by X-ray crystallographic analysis, see later). These pairs of methyl esters 1 and 2 were then hydrolyzed to their acids 4 and 3 respectively. To avoid epimerization, a neutral reagent, trimethylsilyl iodide (TMS-I), was used (W. P. Weber, Silicon Reagents for Organic Synthesis, Springer-Verlag, Berlin, Heidelberg, New York, 1983, page 30–31).

Figure 4:
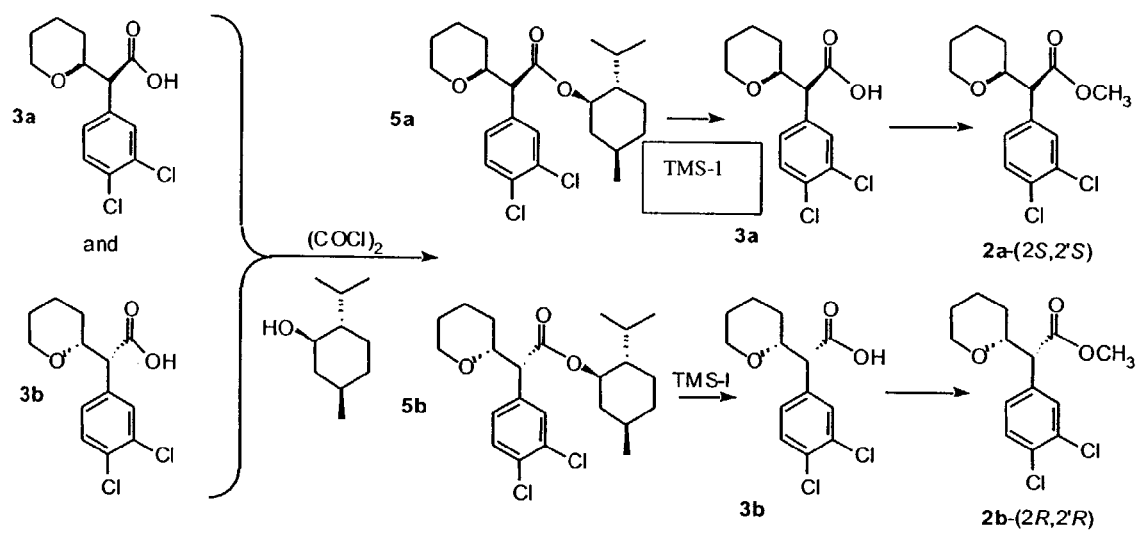
FIG. 4 shows resolution of threo-3,4-dicholorophenyltetrahydropyran-2-yl acetic acid (Scheme 3).

The enantiomeric acid pair (3a and 3b: S,S- and R,R-) resulting from hydrolysis of 2 was then transformed (Scheme 3 in FIG. 4) into diastereomeric menthyl esters (5a and 5b) by treatment of their acid chlorides with optically pure L-menthol. Careful column chromatography then allowed separation of the two newly formed diastereomeric menthyl esters 5a and 5b. These two diastereomerically pure menthyl esters were each separately hydrolyzed (TMS-I) to give the two optically pure acids 3a and 3b.

One of the acids (3a) was crystallized and its absolute configuration was determined by X-ray crystallography. Thus the configuration of 3a was proved to be 2S,2'S. Therefore 3b was proved to be the 2R,2'R enantiomer.

Acids 3a and 3b were then methylated with trimethylsilyl diazomethane to furnish optically pure target molecules 2a-(2S,2'S) (O-1794) and 2b-(2R,2'R) (O-1783).

In contrast, the menthol esters of the diastereomeric pair of acids 4a and 4b proved difficult to separate by column chromatography.

Therefore to obtain the remaining two isomers 1a-(2S,2'R) and 1b-(2R,2'S), the racemic acids (as a mixture of 4a and 4b) from hydrolysis of the mixed methyl esters [1a-(2S,2'R) and 1b-(2R,2'S)] were converted (Scheme 4) to the diastereomeric indanyl esters (6a and 6b) by reaction of their acid chlorides with (S)-(+)-1-indanol. The two indanyl esters were resolved by medium pressure flash column chromatography (ΔR$_f$<0.02). They were then each separately hydrolyzed with trimethylsilyl iodide to provide the two optically pure acids 4a and 4b and methylated with trimethylsilyl diazomethane to furnish the enantiomerically pure methyl esters 1a-(2S,2'R) and 1b-(2R,2'S).

Figure 5:
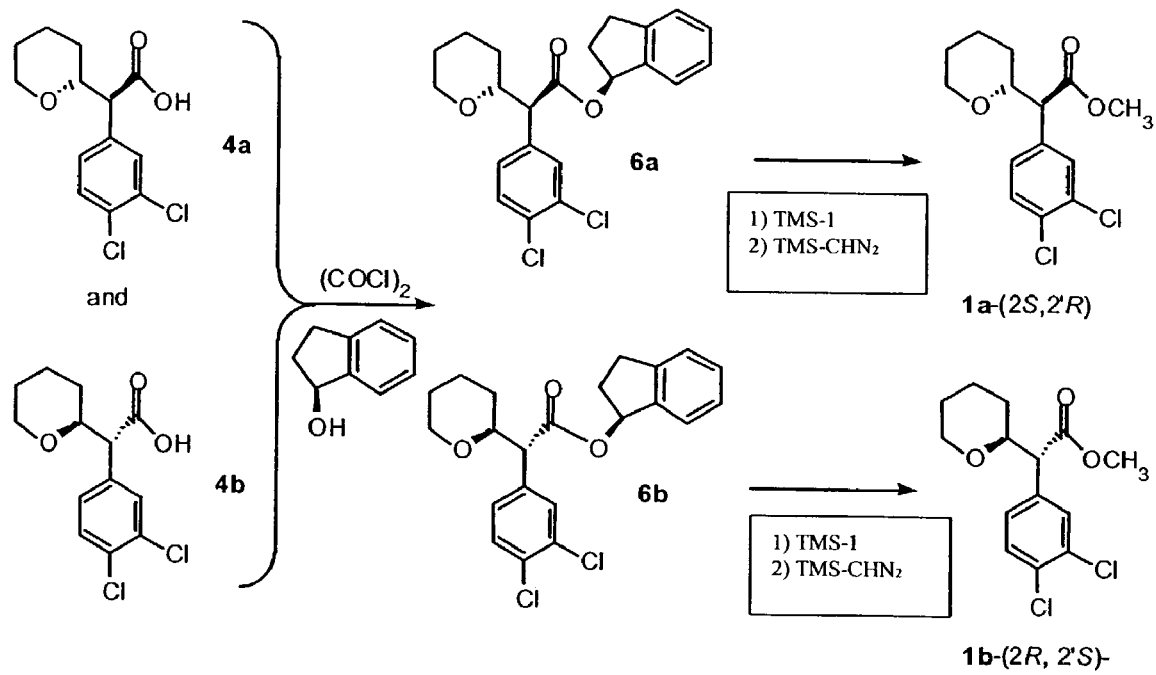
FIG. 5 shows resolution of erythro-3,4-dicholorophenyltetrahydropyran-2-yl acetic acid (Scheme 4).

One of the optically pure acids thus obtained (4b) was reacted, via its acid chloride, with p-nitrophenol to obtain the p-nitrophenylester. This compound was then recrystallized and X-ray crystallographic analysis of this p-nitrophenylester derivative then confirmed its configuration as 2R,2'S. Therefore the methyl ester derived from acid 4b is compound 1b-(2R,2'S) (O-1792). Therefore the remaining enantiomer is 1a-(2S,2'R) (O-1793) (FIG. 5).

Figure 2:
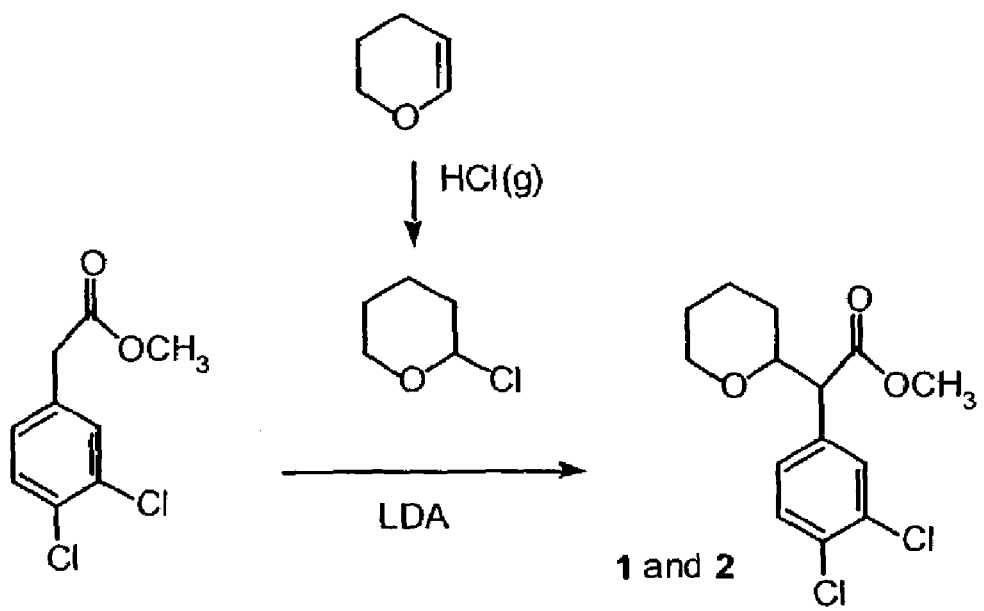
FIG. 2 shows synthesis of aryltetrhydropyranyl methyl esters (Scheme 1).
Figure 2:
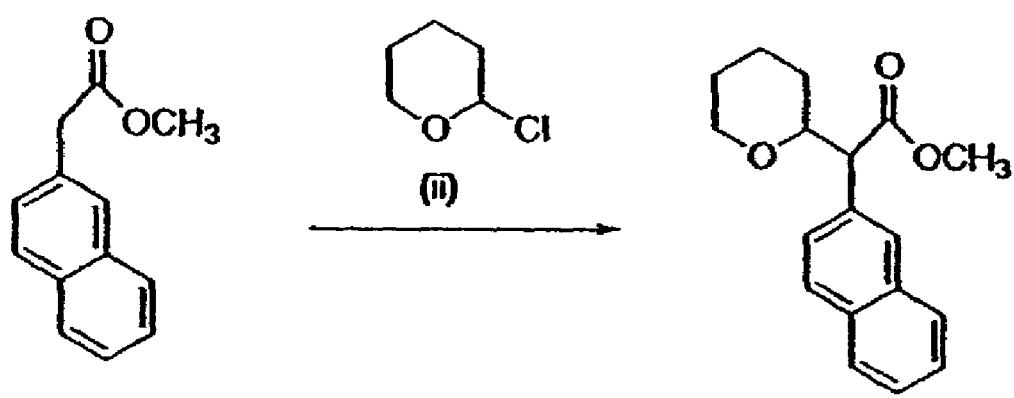
Figure 6:
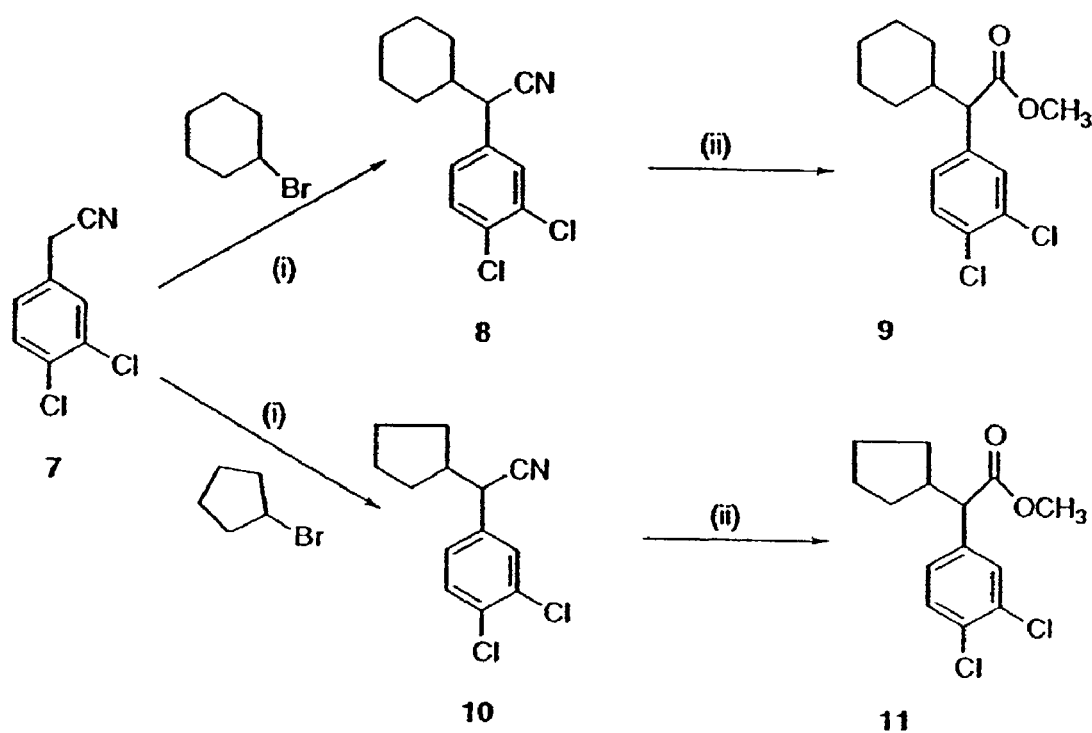
FIG. 6 shows synthesis of 3,4-dicholorophenylcycloalkyl acetic acid methyl esters (Scheme 5).

The diastereomeric mixture of the 2-naphthyl analogs of 1 and 2 were prepared by a similar route (Scheme 1, FIG. 2). Their binding to the DAT and SERT was as follows DAT: IC$_{50}$=0.3 μM; SERT IC$_{50}$=5 μM. The same exchange was conducted in the methylphenidate series. Therefore, carbocyclic analogs of methylphenidate were prepared. Reaction of either cyclohexyl bromide or cyclopentyl bromide with methyl 3,4-dichlorophenylacetate resulted in complex mixtures. In contrast, reaction with the nitrile (Scheme 5, FIG. 6) provided the desired products, which could be hydrolyzed and reesterified to provide the carba analogs. Thus commercially available 7 was reacted with cyclohexyl bromide to provide 8 (or with cyclopentyl bromide to provide 10). Hydrolysis and reesterification then gave 9 and 11 respectively.

TABLE 1

Summary of Binding Data: Inhibition of [$^3$H]WIN 35,428 binding to the dopamine transporter and [$^3$H]citalopram binding to the serotonin transporter in rhesus (macaca mulatta) or cynomolgus monkey (macaca fascicularis) caudate-putamen.

| Compound | Number | DAT IC$_{50}$ (nM) | SERT IC$_{50}$ (nM) |
| --- | --- | --- | --- |
| O-1793 1-erythro | 1a-(2S,2'R) | 736 ± 59 | >10,000 |
| O-1792 d-erythro | 1b-(2R,2'S) | 193 ± 3.5 | >10,000 |
| O-1794 1-threo | 2a-(2S,2'S) | 34 ± 8.6 | 1,655 ± 317 |
| O-1783 d-threo | 2b-(2R,2'R) | 17 ± 1.3 | >10,000 |
| Naphthyl mixture | | 300 | 5,000 |
| | 8 | 127 | 8,000 |

TABLE 1-continued

Summary of Binding Data: Inhibition of [³H]WIN 35,428 binding to the dopamine transporter and [³H]citalopram binding to the serotonin transporter in rhesus (macaca mulatta) or cynomolgus monkey (macaca fascicularis) caudate-putamen.

| Compound | Number | DAT IC$_{50}$ (nM) | SERT IC$_{50}$ (nM) |
|---|---|---|---|
| | 9 | 146 | 12,000 |
| | 10 | 128 | 10,000 |
| | 11 | 47 | 7,000 |

Each value is the mean of 3 or more independent experiments each conducted in different brains and in triplicate. Errors generally do not exceed 15% between replicate experiments. Highest doses tested were generally 10–100 μM. "DAT" = Inhibition of WIN 35,428 binding to the dopamine transporter; "SERT"= Inhibition of citalopram binding to the serotonin transporter Table of Data for Four Enantiomeric Acids

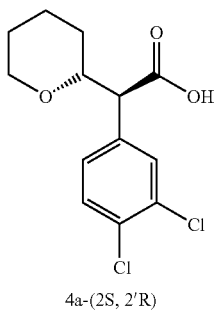

4a-(2S, 2'R)

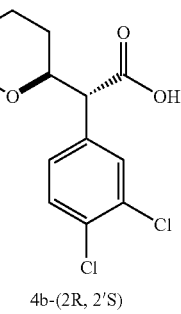

4b-(2R, 2'S)

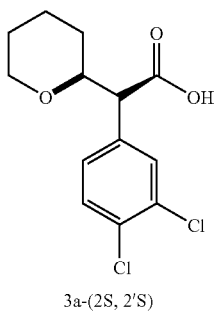

3a-(2S, 2'S)

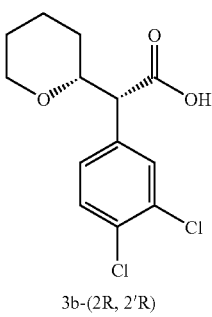

3b-(2R, 2'R)

| Number | 4a | 4b | 3a | 3b |
|---|---|---|---|---|
| Configuration | 2S, 2'R | 2R, 2'S | 2S, 2'S | 2R, 2'R |
| Melting point ° C. | 124.2–125.2 | 124.1–125.1 | 138.9–139.9 | 139.1–140 |
| [Π]$_D^{20}$ (c = 1, CHCl$_3$) | +14.0° | −13.9° | +18.8° | −19.1° |

Experimental Section

NMR spectra were recorded in CDCl$_3$ on a JEOL 300 NMR spectrometer operating at 300.53 MHz for ¹H, and 75.58 MHz for ¹³C. TMS was used as internal standard. Melting points are uncorrected and were measured on a Gallenkamp melting point apparatus. Thin layer chromatography (TLC) was carried out on Baker Si250F plates. Visualization was accomplished with either UV exposure or treatment with phosphomolybdic acid (PMA). Flash chromatography was carried out on Baker Silica Gel 40 mM. Elemental analyses were performed by Atlantic Microlab, Atlanta, Ga. All reactions were conducted under an inert (N2) atmosphere. Optical rotations were measured on a Perkin Elmer 241 Polarimeter. All reactions were conducted under an inert (N2) atmosphere. [³H]WIN 35,428 (2β-carbomethoxy-3β-(4-fluorophenyl)-N-[³H]methyltropane, 79.4–87.0 Ci/mmol) and [³H]citalopram (86.8 Ci/mmol) were purchased from DuPont-New England Nuclear (Boston, Mass.). A Beckman 1801 scintillation counter was used for scintillation spectrometry. Bovine serum albumin (0.1%) was purchased from Sigma Chemicals. (R)-(−)-Cocaine hydrochloride for the pharmacological studies was donated by the National Institute on Drug Abuse [NIDA]. Room temperature is ca. 22° C. TMSI: trimethylsilyl iodide. Yields have not been optimized.

2-Chlorotetrahydropyran.

Dry HCl gas was bubbled through a solution of 3,4-dihydro-2H-pyran (34.1 g, 0.41 mol) in 150 mL of anhydrous ether cooled in a dry-ice/acetone bath for ca. 2 h. Ether was removed by evaporation and fractional distillation of the residue under reduced pressure (bp 36–39° C./18 Torr) furnished 36.75 g (0.31 mol, 75%) of colorless oil. ¹H-NMR (CDCl$_3$) δ 1.4–1.8 (m, 3H), 1.9–2.2 (m, 3H), 3.7–3.8(m, 1H), 3.9–4.1 (m, 1H), 6.27 (t, J=0.54 Hz, 1). This compound was used immediately in the next step.

2-(3,4-Dichlorophenyl)tetrahydropyran-2-yl acetic acid methyl esters, 1 and 2.

n-Butyl lithium (Aldrich, 2.5 M in hexane) (20.8 mL, 52 mmol) was added dropwise to a solution of diisopropylamine (4.8 g, 48 mmol) in anhydrous diethyl ether (100 mL). After stirring at 0° C. for 1.5 h (yellow solution), methyl 3,4-dichlorophenylacetate (9.6 g, 44 mmol) in THF (20 mL) was added dropwise over 30 min; the solution became black. After completion of addition, the solution was stirred for a further 2 h. The round-bottom flask was then immersed in a dry-ice-acetone bath (−78° C.) and the mixture stirred for an additional 20 min.

The mixture was then added dropwise to a solution of 2-chlorotetrahydropyran (5.3 g, 44 mmol) in 40 mL of THF over 1 h and then slowly warmed to room temperature and stirred overnight. Cold (0° C.) 0.5 N hydrochloric acid (104 mL) was added, followed by 400 mL of ethyl acetate. The layers were separated and the organic layer was washed with brine and dried over anhydrous sodium sulfate.

TLC showed two major spots, both of which were UV and PMA active in a ratio of 1:1.4 based on ¹H-NMR.

The crude product was purified by column chromatography using gradient ethyl acetate in hexane (5–15% of ethyl acetate). Total yield was 54%. The first products 1 were obtained as an oil (2.97 g): R$_f$=0.59 (20% ethyl acetate in hexane); ¹H-NMR (CDCl$_3$) δ 7.47 (d, J=2.2 Hz, 1H), 7.38 (d, 8.5 Hz, 1H), 7.21 (dd, J=2.2, 8.5 Hz, 1H), 3.93–3.80 (m, 2H), 3.67 (s, 3H), 3.55 (d, J=11.5 Hz, 1H), 3.40–3.26 (m, 1H), 1.90–1.20 (m, 6H). ¹³C-NMR 171.74, 136.61, 132.37, 131.56, 130.97, 130.26, 128.49, 78.22, 68.95, 56.94, 52.33, 31.67, 29.97, 25.72, 23.24. The second products 2 were obtained as a solid (4.27 g): R$_f$=0.50 (20% ethyl acetate in hexane); mp 65° C.; ¹H-NMR (CDCl$_3$) δ 7.47 (d, J=1.9 Hz, 1H), 7.38 (d, J=8.3 Hz, 1H), 7.19 (dd, J=1.9, 8.3 Hz, 1H), 3.99 (dt); ¹³C-NMR 172.69, 135.45, 132.83, 132.07, 130.63, 128.18, 79.24, 68.91, 57.41, 52.36, 29.16, 25.72, 23.13.

2-(3,4-Dichlorophenyl)tetrahydropyran-2-yl acetic acids, 3a and 3b.

The combined methyl esters 2 (8.5 g, 28 mmol) were dissolved in anhydrous chloroform (10 mL) at room temperature. Trimethylsilyl iodide (14 g, 70 mmol, 2.5 equiv.) was added dropwise with stirring. The mixture was heated at 80° C. overnight. It was then cooled to room temperature and the volatiles were evaporated. Aqueous sodium thiosulfate solution (1%) and 25 mL of diethyl ether were added to the residue and the two layers were separated. The colorless ether phase was dried over sodium sulfate, filtered, and concentrated. The residue was purified by column chromatography (30% ethyl acetate in hexane, then 50% ethyl acetate in hexane). The acids 3a and 3b were obtained (5.2 g, 65% combined yield). $^1$H-NMR (CDCl$_3$) δ 7.43 (d, J=2.2 Hz, 1H), 7.40 (d, J=8.5 Hz, 1H), 7.21 (dd, J=8.3, 2.2 Hz, 1H), 3.98 (dd, J=10.8, 2.3 Hz, 1H), 3.87 (m, 1H), 3.61 (d, J=7.4 Hz, 1H), 3.4 (m, 1H), 1.95–1.20 (m, 6H).

2-(3,4-Dichlorophenyl)tetrahydropyran-2-yl acetic acid menthyl esters, 5a and 5b.

The combined 3,4-dichlorophenyl tetrahydropyran-2-yl acetic acids 3a and 3b (0.86 g, 3.0 mmol) were dissolved in 80 mL of anhydrous dichloromethane. Three drops of DMF were added, followed by the dropwise addition of oxalyl chloride (0.58 g, 4.8 mmol, 1.6 equiv.) at room temperature. The solution was stirred for 3 h. Volatiles were removed and anhydrous THF (75 mL) was introduced followed by the addition of pyridine (0.5 g). L-Menthol (0.47 g, 3.0 mmol) in THF (5 mL) was added dropwise. The reaction mixture was stirred overnight and then poured into 100 mL of water. Ether (150 mL) was added. The layers were separated and the aqueous phase was further extracted with ether. The combined organic phase was washed with brine and dried over sodium sulfate, filtered and concentrated.

TLC (10% ethyl acetate in hexane) showed two major spots (R$_f$ 0.54 and 0.50). After column chromatography (hexane 800 mL, 1% ethyl acetate in hexane 800 mL, and finally 3% ethyl acetate 800 mL), 400 mg of the first product 5a: R$_f$=0.54 (10% ethyl acetate/hexanes); $^1$H-NMR (CDCl$_3$) 7.50 (d, J=2.19 Hz, 1H), 7.38 (d, J=8.25 Hz, 1H), 7.22 (dd, J=2.19, 8.25 Hz, 1H), 4.70 (td, J=4.38, 11.04 Hz, 1H), 3.94 (dt, J=2.19, 11.28 Hz, 1H), 3.79 (td, J=2.19, 10.44 Hz, 1H), 3.45 (td, J=2.73, 9.06 Hz, 1H), 3.46 (d, J=9.87 Hz, 1H), 2.0–0.9 (m, 15H), 0.88 (d, J=7.68 Hz, 3H), 0.86 (d, J=6.6 Hz, 3H), 0.72 (d, J=6.87 Hz, 3H); $^{13}$C-NMR (CDCl$_3$) 171.76, 135.69, 132.55, 131.70, 130.55, 130.37, 120.21, 79.39, 74.93, 68.53, 57.83, 47.03, 40.53, 34.20, 31.37, 28.96, 25.70, 23.07, 21.96, 20.86, 15.86; and 425 mg of a second product 5b was obtained (65% combined yield): R$_f$=0.50 (10% ethyl acetate/hexanes); $^1$H-NMR (CDCl$_3$) 7.47 (d, J=2.19 Hz, 1H), 7.38 (d, J=8.22 Hz, 1H), 7.20 (dd, J=2.19, 8.22 Hz, 1H), 4.68 (td, J=4.41, 10.98 Hz, 1H), 3.94 (dt, J=2.19, 11.25 Hz, 1H), 3.83 (td, J=2.19, 10.17 Hz, 1H), 3.44 (td, J=3.03, 12.10 Hz, 1H), 3.45 (d, J=9.90 Hz, 1H), 2.0–0.9 (m, 15H), 0.88 (d, J=6.66 Hz, 3H), 0.78 (d, J=6.87 Hz, 3H), 0.61 (d, J=6.87 Hz, 3H); $^{13}$C-NMR (CDCl$_3$) 171.15, 135.76, 132.56, 131.72, 130.52, 130.42, 128.08, 78.86, 75.03, 68.61, 58.27, 47.15, 40.72, 34.21, 31.40, 29.02, 25.79, 25.62, 23.23, 23.07, 21.96, 20.67, 15.91.

2-(3,4-Dichlorophenyl)tetrahydropyran-2-yl acetic acid, 4a and 4b.

The methyl ester 1 (4.4 g, 14.5 mmol) was dissolved in anhydrous chloroform (60 mL) and Me$_3$SiI (10.0 g) was added. The mixture was heated in an oil bath at 80° C. After 20 h, $^1$H-NMR showed the reaction was only 25% complete. The reaction mixture was then heated for an additional 4 days whereupon it was cooled to room temperature and ice (20 g) was added, followed by addition of Na$_2$SO$_3$ solution (0.5N) to the point that almost no red color remained. The layers were separated and the aqueous phase was extracted with CH$_2$Cl$_2$ (80 mL×2). The combined organic extracts were dried over Na$_2$SO$_4$. The crude product was purified by column chromatography (200 g of silica gel, CH$_2$Cl$_2$, 3 L, 3% MeOH in CH$_2$Cl$_2$, 3 L) and 3.4 g of pure product, 4a and 4b, was obtained (83% yield). $^1$H-NMR (CDCl$_3$) δ 7.47 (d, J=2.19 Hz, 1H), 7.40 (d, J=8.52 Hz, 1H), 7.21 (dd, J=8.52, 2.19 Hz, 1H), 3.97 (dd, J=10.71, 2.22 Hz, 1H), 3.60 (d, J=7.14 Hz, 1H), 3.45–3.36 (m, 1H), 1.90–1.20 (m, 6H).

2-(3,4-Dichlorophenyl)tetrahydropyran-2-yl acetic acid indanyl esters, 6a and 6b.

The enantiomeric pair of 2-(3,4-dichlorophenyl) tetrahydropyran-2-yl acetic acids 4a and 4b (4.0 g, 13.83 mmol) was dissolved in anhydrous CH$_2$Cl$_2$ (80 mL) and 4 drops of DMF were added. Oxalyl chloride (3.5 g, 27.7 mmol, 2 equiv.) was added dropwise while the solution was vigorously stirred. Evolution of bubbles was observed. After completion of addition, the light yellow solution was stirred at room temperature for a further 2.5 h.

Solvent was removed by evaporation and the residue was dried in vacuo. (S)-(+)-1-Indanol (1.87 g, 13.9 mmol) was dissolved in anhydrous THF (25 mL) and dry pyridine (25 mL) and cooled to 0° C. The acid chloride, prepared as above, in THF (50 mL) was added dropwise to this cold, stirred solution and stirred at 0° C. for 2 h, and then warmed up to room temperature and stirred overnight. $^1$H-NMR data show that the ratio of 6a (R$_f$=0.71 in 10% EtOAc, 90% hexane, developed 3 times) to 6b (R$_f$=0.67) was 4:5 based on the peaks at 3.53 ppm and 3.54 ppm. The mixture was evaporated to remove most of the solvent. The residue was redissolved in a mixture of hexane/ethyl acetate (10:5) (80 mL) to provide a light yellow suspension. The mixture was loaded on a short silica gel pad and washed with hexane/ethyl acetate (10:1). The product fractions were combined and evaporated and dried. A light yellow oil was obtained (4.0 g, 71.4% crude yield). It was purified by column chromatography (300 g of silica gel, 0.4% of ethyl acetate, 99.6% of hexane, 4 L, then 0.8% ethyl acetate in hexane, 5 L). A total of 0.6 g of 6a, 1.0 g of a mixture of 6a and 6b, and 0.5 g of 6b were obtained. $^1$H-NMR (CDCl$_3$) 6a: δ 7.49 (d, J=2.19 Hz, 1H), 7.39–7.10 (m, 6H), 6.20 (m, 1H), 3.92–3.80 (m, 2H), 3.53 (d, J=8.79 Hz, 1H), 3.34–3.25 (m, 1H), 3.1–3.0 (m, 1H), 2.9–2.8 (m, 1H), 2.5–2.4 (m, 1H), 2.0–1.1 (m, 6H). $^{13}$C-NMR 171.07, 144.31, 140.56, 136.56, 132.19, 131.39, 130.90, 130.08, 129.04, 128.50, 126.73, 125.34, 124.85, 79.09, 78.16, 68.80, 57.08, 31.99, 30.13, 29.81.

6b: $^1$H-NMR (CDCl$_3$) 7.47 (d, J=2.19 Hz, 1H), 7.37 (d, J=8.25 Hz, 1H), 7.31–7.18 (m, 5H), 6.17 (m, 1H), 3.92–3.80 (m, 2H), 5.53 (d, J=8.52 Hz, 1H), 3.40–3.27 (m, 1H), 3.14–3.03 (m, 1H), 2.95–2.82 (m, 1H), 2.59–2.40 (m, 1H), 2.2–1.2 (m, 6H). $^{13}$C-NMR 171.09, 144.28, 140.37, 136.48, 132.16, 131.37, 130.95, 130.07, 129.05, 128.51, 126.72, 125.28, 124.82, 79.18, 78.16, 68.84, 57.04, 32.23, 30.15, 29.81, 25.61, 23.14.

Hydrolysis of Menthyl (5a and 5b) and Indanyl (6a and 6b) Esters (General Procedure)

The hydrolyses of the menthyl and indanyl esters to the corresponding acids was conducted similarly and yields were in a range of 38–55%. The procedure is exemplified for 6a below.

2S-(3,4-Dichlorophenyl)tetrahydropyran-2'R-yl acetic acid, 4a-2S,2'R.

The indanyl ester 6a (1.65 g, 4.07 mmol) was dissolved in anhydrous carbon tetrachloride (25 mL). Trimethylsilyl iodide (2.4 g, 12 mmol, 3 equiv.) was added. The mixture was heated at 90° C. with stirring for 18 h.

The reaction mixture was cooled to 0° C., cold water (20 mL) and dichloromethane (50 mL) were added and layers were separated. The aqueous phase was washed with dichloromethane (50 mL×2). The combined organic phases were dried over anhydrous sodium sulfate and filtered. The filtrate was evaporated to dryness. The residue was purified by column chromatography (10% methanol in dichloromethane) and 600 mg of product 4a was obtained (55% yield). Mp 124.2–125.2° C. $[\alpha]_D^{20}$=14.0° (c=1, CHCl$_3$); $^1$H-NMR (CDCl$_3$) δ7.47 (d, J=2.19 Hz, 1H), 7.40 (d, J=8.52 Hz, 1H), 7.21 (dd, J=8.52, 2.19 Hz, 1H), 3.97 (dd, J=10.77, 2.22 Hz, 1H), 3.92–3.83 (m, 1H), 3.60 (d, J=7.14 Hz, 1H), 3.45–3.36 (m, 1H), 1.9–1.2 (m, 6H), 2R-(3,4-Dichlorophenyl)tetrahydropyran-2′S-yl acetic acid, 4b-2R,2′S.

Acid 4b was obtained from 6b as described above for 4a. $^1$H-NMR data are identical 4a. Mp 124.1–125.1° C.$[\alpha]_D^{20}$=−13.9° (c=1, CHCl$_3$). $^{13}$C-NMR (CDCl$_3$) 176.67, 135.53, 132.36, 131.80, 131.18, 130.21, 128.74, 77.82, 68.95, 56.60, 29.56, 25.49, 23.04

2S-(3,4-Dichlorophenyl)tetrahydropyran-2′S-yl acetic acid, 3a-2S,2′S.

Acid 3a was obtained from 5a as described for 4a above. M.p. 138.9–139.9° C. $[\alpha]_D^{20}$ =18.8° (c=1, CHCl$_3$). $^1$H-NMR (CDCl$_3$) δ7.45 (d, J=1.95 Hz, 1H), 7.40 (d, J=8.25 Hz, 1H), 7.18 (dd, J=8.25, 2.22 Hz, 1H), 4.06 (dt, J=11.22, 1.92 Hz, 1H), 3.9–3.7 (m, 1H), 3.52 (d, J=9.33 Hz, 1H), 3.50 (td, J=11.25, 3.3 Hz, 1H), 1.9–1.1 (m, 6H).

2R-(3,4-Dichlorophenyl)tetrahydropyran-2′R-yl acetic acid, 3b-2R,2′R.

Acid 3b was obtained from 5b as described for 4a above. NMR data are identical to acid 3a. Mp 139.1–140.1° C. $[\alpha]_D^{20}$=19.1° (c=1, CHCl$_3$)

2-(3,4-Dichlorophenyl)tetrahydropyran-2-yl acetic acid methyl esters, 1a, 1b, 2a, 2b (General Procedure)

Acids 3a, 3b, 4a, 4b, were methylated with trimethylsilyl diazomethane to obtain the methyl esters. The following procedure is representative.

2S-(3,4-Dichlorophenyl)tetrahydropyran-2′R-yl acetic acid methyl ester, 1a-2S, 2′R.

Acid 4a-2S, 2′R (90 mg, 0.31 mmol) was dissolved in anhydrous toluene (4 mL) and anhydrous methanol (1 mL). Trimethylsilyl diazomethane (0.63 mL, 2.0M in hexane, 1.25 mmol, 4 equiv) was slowly added while stirring at room temperature and the mixture was stirred for 5 h. Volatiles were removed in vacuo. The residue (100 mg) was purified by column chromatography (2% ethyl acetate in hexane) to provide 1a-2S, 2′R as an of oil (61 mg, 64% yield). $^1$H-NMR (CDCl$_3$) δ 7.47 (d, J=2.19 Hz, 1H), 7.39 (d, J=8.25 Hz, 1H), 7.22 (dd, J=8.25, 2.19 Hz, 1H), 3.92–3.81 (m, 1H), 3.68 (s, 3H), 3.56 (d, J=8.52 Hz, 1H), 3.39–3.20 (m, 1H), 1.9–1.1 (m, 6H). Anal. calcd. for C$_{14}$H$_{16}$O$_3$Cl$_2$=C 55.46, H 5.32, Cl 23.39; found: C 55.56, H 5.42, Cl 23.51.

2R-(3,4-Dichlorophenyl)tetrahydropyran-2′S-yl acetic acid methyl ester, 1b-2R, 2′S.

Methyl ester 1b was prepared from 4b as described above for 1a. $^1$H-NMR data identical to those of 1a. Anal. calcd. for C$_{14}$H$_{16}$O$_3$Cl$_2$: C 55.46, H 5.32, Cl 23.39; found: C 55.55, H 5.38, Cl 23.51.

2S-(3,4-Dichlorophenyl)tetrahydropyran-2′S-yl acetic acid methyl ester, 2a-2S, 2′S.

Methyl ester 2a was prepared from 3a as described above for 1a. $^1$H-NMR (CDCl$_3$) δ 7.48 (d, J=1.92 Hz, 1H), 7.39 (d, J=8.25 Hz, 1H), 7.25 (dd, J=8.25, 2.19 Hz, 1H), 4.03–3.95 (m, 1H), 3.84 (td, J=10.71, 2.19 Hz, 1H), 3.70 (s, 3H), 3.50 (d, J=9.9 Hz, 1H), 3.47 (td, J=11.34, 3.3 Hz, 1H), 1.9–1.0 (m, 6H). Anal. calcd. for C$_{14}$H$_{16}$O$_3$Cl$_2$: C 55.46, H 5.32, Cl 23.39; found: C 55.63, H 5.43, Cl 23.47, 2R-(3,4-Dichlorophenyl)tetrahydropyran-2′R-yl) acetic acid methyl ester, 2b-2R, 2′R.

Methyl ester 2b was prepared from 3b as described above for 1a. $^1$H-NMR data are identical to those of 2a. Anal. calcd. for C$_{14}$H$_{16}$O$_3$Cl$_2$: C 55.46, H 5.32, Cl 23.39, found: C 55.53, H 5.38, Cl 23.27.

2R-(3,4-Dichlorophenyl)tetrahydropyran-2′S-yl acetic acid p-nitrophenyl ester, (p-Nitrophenyl ester of 4b-2R,2′S).

Compound 4b-(2R,2′S) obtained from 1b-(2R,2S′) (100 mg) was dissolved in anhydrous dichloromethane (5 mL). One drop of DMF was added. Oxalyl chloride (0.14 g) was slowly added and the reaction mixture was stirred at room temperature for 3 h. Solvent was then removed by evaporation.

4-Nitrophenol (56 mg) was dissolved in anhydrous THF (3 mL) and pyridine (85 mg) was added. The mixture was cooled to 0° C. in an ice-water bath. To this cooled, stirred solution was added the acid chloride prepared above in 2 mL of THF over 10 min. The mixture was warmed up to room temperature and stirred overnight. The crude product was purified by column chromatography (0.6% ethyl acetate in hexane). The product (0.105 g) was obtained as a gummy material (75% yield). R$_f$=0.46 (20% ethyl acetate in hexane). $^1$H-NMR (CDCl$_3$) δ 8.3–8.2 (m, 2H), 7.55 (d, J=2.19 Hz, 1H), 7.45 (d, J=8.25 Hz, 1H), 7.32–7.18 (m, 3H), 4.07–3.91 (m, 2H), 3.83 (d, J=7.41 Hz, 1H), 3.46–3.37 (m, 1H), 2.0–1.2 (m, 6H). The gum was recrystallized from pentane. X-ray structural analysis showed the enantiomerically pure p-nitrophenyl ester of 4b to be of 2R,2′S configuration.

2,2-(3,4-dichlorophenyl)cycloalkyl acetic acid methyl ester.

The following procedure is representative. To a stirred solution of t-BuOK (11.0 mL, 1.0 M in THF), a solution of 3,4-dichlorophenyl acetonitrile (1.86 g, 10.0 mmol) in THF (20 mL) was slowly added. The mixture was stirred for 0.5 h, and cyclopentyl bromide (1.57 g, 10.5 mmol) in THF (10 mL) was added. The dark brown solution was stirred at 22° C. for 1 h and then heated to reflux overnight. After cooling it was transferred to a separatory funnel and EtOAc (200 mL) and water (150 mL) were added. The organic phase was separated and washed consecutively with H$_2$O and brine, dried (Na$_2$SO$_4$), concentrated and purified by column chromatography (1–2% EtOAc in hexane) to yield 10 (α-cyclopentyl-3,4 -dichlorobenzylcyanide) as an oil (1.78 g; 70%). $^1$H NMR δ 7.45 (d, 1H), 7.43 (d, 1H), 7.18 (dd, 1H), 3.69 (d, J=7.7 Hz, 1H), 2.4–1.2 (m, 9H). Anal. (C$_{13}$H$_{13}$NCl$_2$) C, H, Cl.

The nitrile 10 (α-cyclopentyl-3,4-dichlorobenzylcyanide) (1.2 g, 4.7 mmol) was dissolved in HCl-methanol solution (65 mL, 10.3 M), sealed with a stopper and stirred at 22° C. for 2 days. 6N Hydrochloric acid (30 mL) was slowly added to the mixture which was stirred for 10 min and evaporated to dryness. A further 50 mL of HCl-methanol solution (10.3 M) was added and stirring continued for 4 days. An additional 30 mL of 6N hydrochloric acid was added and the mixture brought to reflux for 2 days. After cooling, EtOAc (200 mL) and water (150 mL) were added. The organic phase was washed with water, followed by brine, dried (Na$_2$SO$_4$) and concentrated. The oil obtained (R$_f$ 0.45, 10% EtOAc in hexane,) was purified by column chromatography (0.5%–1% EtOAc in hexane) to provide α-cyclopentyl-3,4-dichlorobenzylcyanide and α-cyclopentyl-3,4-dichlorophenylcyclohexyl acetic acid methyl ester (11) as a colorless oil (1.1 g, 82%). $^1$H NMR δ 7.45 (d, 1H), 7.35 (d, 1H), 7.19 (dd, 1H), 3.66 (s, 3H), 3.23 (d, J=11.3 Hz, 1H), 2.6–2.4, m, 1H), 2.0–1.8 (m, 1H), 1.8–0.8 (m, 7H). Anal. ($C_{14}H_{16}O_2Cl_2$) C, H, Cl.

α-cyclohexyl-3,4-dichlorobenzylcyanide (8).

(46%), $^1$H NMR δ 7.45 (d, 1H), 7.39 (d, 1H), 7.42 (dd, 1H), 3.60 (d, J=6.3 Hz, 1H), 1.9–1.1 (m, 11H). Anal. ($C_{14}H_{15}NCl_2$) C, H, Cl.

α-cyclohexyl-3,4-dichlorophenylcyclohexyl acetic acid methyl ester (9).

(40%), $^1$H NMR δ 7.43 (d, 1H), 7.38 (d, 1H), 7.28 (dd, 1H), 3.66 (s, 3H), 3.19 (d, J=10.7 Hz, 1H), 2.1–0.7 (m, 11H). Anal. ($C_{14}H_{18}O_2Cl_2$) C, H, Cl.

(2-Naphthyl)-(tetrahydropyran-2-yl) acetic acid methyl esters.

2-Naphthyl acetic acid (24.5 g, 0.132 mol) was dissolved in methanol (180 mL) and concentrated $H_2SO_4$ (2 mL) was added. The mixture was warmed to 45° C. and stirred for 18 h. It was then cooled to 22° C. and neutralized with $NaHCO_3$ to pH 7. Methanol was removed by evaporation, and $H_2O$ (150 mL) was added. It was extracted with EtOAc (300 mL×3). The combined organic phase was dried ($Na_2SO_4$), filtered and evaporated to dryness. Distillation (130° C., 0.5 mm Hg. 84%) furnished a white solid (22.0 g). $^1$H NMRδ 7.88–7.78 (m, 3H), 7.72 (s, 1H), 7.53–7.39 (m, 3H), 3.80 (s, 2H), 3.71 (s, 3H). The ester prepared above (2.0 g, 10.0 mmol) was dissolved in anhydrous THF (15 mL) and added dropwise to a cold (0° C.) LDA solution (5.0 mL, 2.0 M in heptane:THF:ethyl benzene 1:2:1.5) and stirred for 2 h at 0° C. The mixture was cooled to −78° C., and 2-chlorotetrahydropyran (1.2 g, 10 mmol) in THF (5 mL) was added dropwise. The reaction mixture was stirred at −78° C. for 1 h, then slowly warmed to 22° C. and stirred overnight (17 h). THF was removed in vacuo and $H_2O$ (20 mL) was added. The crude product was extracted with $Et_2O$ (50 mL×3). The combined $Et_2O$ phases were dried ($Na_2SO_4$), filtered, and evaporated. The light brown oil (3.2 g) was purified by column chromatography (1% EtOAc in hexane) to provide the product (0.50 g, 18%). $^1$H NMR δ 7.88–7.78 (m, 4H), 7.53–7.41 (m, 3H), 4.10–3.98 (m, 2H), 3.73 (s, 1H), 3.70 (s, 3H), 3.53 (td, J=11.6, 3.1 Hz, 1H), 1.9–1.0 (m, 6H), Anal. ($C_{18}H_{20}O_3 \cdot 0.4H_2O$) C, H, Cl.

Single-Crystal X-ray Analysis of (2S,2'S)-(3,4-Dichlorophenyl)-(tetrahydropyran-2-yl) acetic acid (3a)

Monoclinic crystals of 3a were obtained from pentane. A representative crystal was selected and a data set was collected at room temperature. Pertinent crystal, data collection and refinement parameters: crystal size, 0.56×0.40× 0.22 mm; cell dimensions, a=11.988 (1) Å, b=8.222 (1) Å, c=14.539 (1) Å, α=90°, β=104.35(1)°, γ=90°; formula, $C_{13}H_{14}Cl_2O_3$; formula weight=289.14; volume=1388.4 (2) Å$^3$; calculated density=1383 Mg/m$^{-3}$; space group=P2(1); number of reflections=2231 of which 2048 were considered independent ($R_{int}$=0.0185). Refinement method was full-matrix least-squares on F$^2$. The final R-indices were [I>2σ (I)] R1=0.0465, wR2=0.1263.

Single-Crystal X-ray Analysis of (2R,2'S)-(3,4-Dichlorophenyl)-(tetrahydropyran-2-yl) acetic acid (4b) p-nitrophenyl ester.

Orthorhombic crystals of the purified p-nitrophenyl ester of 4b were obtained from 90% hexane/10% EtOAc. A representative crystal was selected and a data set was collected at room temperature. Pertinent crystal, data collection and refinement parameters: crystal size, 0.49×0.08× 0.06 mm; cell dimensions, a=6.844 (1) Å, b=11.516 (2) Å, c=23.922 (6) Å, α=90°, β=90°, γ=90°; formula, $C_{19}H_{17}Cl_2NO_5$; formula weight=410.24; volume= 1885.3 (7) Å$^3$; calculated density=1.445 Mg/m$^{-3}$; space group=P2$_1$2$_1$2$_1$; number of reflections=1580 of which 1529 were considered independent ($R_{int}$=0.0215). Refinement method was full-matrix least-squares on F$^2$. The final R-indices were [I>2σ(I)] R1=0.0504, wR2=0.1190.

III. In Vitro Binding Assays

The affinities and transporter selectivities of the drugs were assessed in brain tissue of adult cynomolgus or rhesus monkey (*Macaca fasicularis* or *Macaca Mulatta*). Caudate-putamen was the source of the dopamine and serotonin transporters. The dopamine transporter affinity was measured with [3H]WIN 35,428 ([3H]CFT), the serotonin transporter was measured with [3H]citalopram and the norepinephrine transporter was measured with [3H]nisoxetine. Affinities of selected compounds were also measured at the human dopamine transporter in HEK-293 cells expressing the human dopamine transporter (hDAT).

A. Brain Tissue Preparation.

Brain tissue was harvested from adult male and female cynomolgus (*Macaca fasicularis*) or rhesus (*Macaca Mulatta*) monkeys euthanized in the course of other research or after spontaneous death. Tissue was stored in the brain bank at the New England Regional Primate Research Center at −85° C. The caudate-putamen (approximately 1.5 g) was dissected from coronal sections of brain. Each caudate-putamen was homogenized and used separately for dopamine and serotonin transporter assays. Prior to homogenization, the thalamus from two brains was pooled and membranes were prepared as described previously for norepinephrine transporter assays (Madras et al., *Synapse*, 22:231–232, 1998; Madras et al., *Synapse*, 24:340–348, 1996). Briefly, the tissue was homogenized in 10 volumes (w/v) of ice-cold Tris.HCl buffer (50 mM, pH 7.4 at 0–4° C.) and centrifuged at 38,700×g for 20 min in the cold. The resulting pellet was resuspended in 40 volumes of buffer, and the entire wash procedure was repeated twice. The membrane suspension (25 mg original wet weight of tissue/ml) was diluted to 12 mg/ml in buffer just prior to assay and dispersed with a Brinkmanm polytron (setting #5) for 15 sec. Preliminary experiments demonstrated that tissue washing enhanced [$^3$H]WIN 35,428 (CFT) binding in tissue homogenates or tissue sections (Canfield et al., Synapse 6:189–194, 1990; Madras, et al., *Mol. Pharmacol.* 36:518–524, 1989). All experiments were conducted in triplicate and each experiment was repeated in 2–4 individual tissue preparations.

B. Dopamine Transporter Assay to Measure Affinity of Candidate Compounds

Competition experiments to determine the affinities of drugs at [$^3$H]WIN 35,428 (CFT) binding sites at the dopamine transporter were conducted using procedures previously reported (Madras et al., *Mol. Pharmacol.* 36:518–524, 1989). Stock solutions of water-soluble drugs were dissolved in water or buffer and stock solutions of other drugs were made in a range of ethanol/HCl solutions. Several of the drugs were sonicated to promote solubility. The stock solutions were diluted serially in the assay buffer and added (0.2 ml) to the assay medium as described above. Each serial dilution in buffer was examined to ensure that the relatively water-insoluble compounds did not precipitate out. Affinities of drugs for the dopamine transporter were conducted as follows:

Affinities of drugs for the dopamine transporter, labeled by [$^3$H]CFT (Specific activity: approximately 80 Ci/mmol, NEN) were determined in experiments by incubating tissue with a fixed concentration of [$^3$H]CFT and a range of concentrations of unlabeled test drug. The assay tubes received, in Tris.HCl buffer (50 mM, pH 7.4 at 0–4° C.;

NaCl 100 mM), at a final assay concentration: [$^3$H]CFT (1 nM, 0.2 ml); test drug (1 μM–100 TM, 0.2 ml or buffer), membrane preparation (0.2 ml, 1 mg original wet weight of tissue/ml). The 2 h, incubation (0–4° C.) was initiated by addition of membranes and terminated by rapid filtration over Whitman GFB glass fiber filters pre-soaked for 1 hour in 0.1% bovine serum albumin (Sigma Chem. Co.). The filters were washed twice with 5 ml Tris.HCl buffer (50 mM), incubated overnight at 0–4° C. in scintillation floor (Beckman Ready-Value, 5 ml) and radioactivity was measured by liquid scintillation spectrometry. Cpm were converted to dpm following determination of counting efficiency (49–53%) of each vial by external standardization. Total binding was defined as [$^3$H]CFT bound in the presence of ineffective concentrations of test drug (0.1–10 TM). Non-specific binding was defined as [$^3$H]CFT bound in the presence of an excess (30 TM) of (–)cocaine. Specific binding was the difference between the two values. In the caudate-putamn total binding of [$^3$H]CFT ranged from 1,500–3,500 dpm, and specific binding was approximately 90% of total.

The affinity of ([$^3$H]CFT) for the dopamine transporter was determined in experiments by incubating tissue with a fixed concentration of [$^3$H]CFT and a range of concentrations of unlabeled CFT. The assay tubes received, in Tris.HCl buffer (50 mM, pH 7.4 at 0–4° C.; NaCl 100 mM), the following constituents at a final assay concentration: CFT, 0.2 ml (1 pM–100 or 300 nM), [$^3$H]CFT (0.3 nM); membrane preparation 0.2 ml (4 mg original wet weight of tissue/ml).

C. Serotonin Transporter Assay to Measure Affinity of Candidate Compounds

The serotonin transporter was assayed in caudate-putamen membranes using similar assay conditions as for the dopamine transporter. The assays were conducted sideby-side to ensure that comparisons of the relative potencies of the drugs at the two transporters were similar. The affinity of drugs for the serotonin transporter labeled by [$^3$H]citalopram (spec. act.: approximately 85 Ci/mmol, NEN) was determined in experiments by incubating tissue with a fixed concentration of [$^3$H]citalopram and a range of concentrations of drug. Assays were conducted in Tris-HCl buffer containing NaCl (100 mM) and the following constituents: [$^3$H]citalopram (1 nM, 0.2 ml), test drug (1 pM–100 TM, 0.2 ml) and tissue (0.2 ml, 3 mg/ml original wet tissue weight). The 2 h incubation (0–4° C.) was initiated by addition of membranes and terminated by rapid filtration over Whatman GF/B glass fiber filters pre-soaked 1 hour in 0.1% polyethyleneimine. The filters were washed three times with 5 ml Tris.HCl buffer (50 mM), and the remaining steps were carried out as described above. Total binding was defined as [$^3$H]citalopram bound in the presence of ineffective concentrations of unlabeled citalopram (1 pM) or the test compounds. Non-specific binding was defined as [$^3$H]citalopram bound in the presence of an excess (10 TM) of fluoxetine. Specific binding was the difference between the two values. Cpm were converted to dpm following determination of counting efficiency (>45%) of each vial by external standardization.

D. Norepinephrine Transporter Assay

The norepinephrine transporter was assayed in thalamus membranes using conditions similar to those for the serotonin transporter and adapted from whole rat brain (Gehlart et al., *J. Neurochem.* 64:2792, 1995). The affinity of [$^3$H] nisoxetine (spec. act.: 74 Ci/mmol, NEN) for the norepinephrine transporter was determined in experiments by incubating tissue with a fixed concentration of [$^3$H]nisoxetine and a range of concentrations of unlabeled nisoxetine. The assay tubes received the following constituents at a final assay concentration: nisoxetine or drug (0.2 ml; 1 pM–300 TM), [$^3$H]nisoxetine (0.2 ml; 0.6 nM); membrane preparation (0.2 ml; 4 mg original wet weight of tissue/ml). The buffer in the assay medium was Tris-HCl: 50 mM, pH 7.4 at 0–4° C.; NaCl 300 mM. The 16 h incubation at 0–4° C. was initiated by addition of membranes and terminated by rapid filtration over Whatman GF/B glass fiber filters pre-soaked in 0.3% polyethyleneimine for 1 h. The remaining steps are described above. Total binding was defined as [$^3$H]nisoxetine bound in the presence of ineffective concentrations of drug. Non-specific binding was defined as [$^1$H]nisoxetine bound in the presence of an excess (10 TM) of desipramine. Specific binding was the difference between the two values.

E. Dopamine Transporter Assay in Cell Lines Expressing the Human Dopamine Transporter HDAT Cell Line (HEK-293) Preparation.

A full length human DAT cDNA isolated from a human substantia nigra cDNA library was ligated into pcDNA3.1 (InVitrogen), resulting in an human dopamine transporter expression vector, peDNA3.1/hDAT. HEK293 cells were grown in DMEM (BRL) supplemented with 10% fetal bovine serum (BR-L), 100 U/ml penicillin, 100:g streptomycin (BRL), and 0.1 mm non-essential amino acids (BRL), at 5% $CO_2$ in a 37° C. water-jacketed incubator. pcDNA3.1/hDAT (2 Tg) was transfected into HEK-293 cells with Lipofectamine Reagent (BRL) according to the manufacturer's protocol. Following geneticin selection selection, single cells were replated into 12 well plates. At confluence, monoclonal cell lines were replated and assayed for [$^3$H].

The clone that displayed the highest dopamine uptake was selected and expanded for study of dopamine uptake.

Affinities of Drugs for Blocking [$^3$H]Dopamine Transport in HEK-293 Cells Expressing the Human Dopamine Transporter (hDAT).

Low passage number cells (<25) plated at 80–90% confluency in 145 mm dishes were used for [$^3$H]dopamine transport studies. The medium was removed by aspiration, and cells were washed with Tris-Hepes buffer, pH 7.4 at 25° C. (Tris base: 5 mM, Hepes: 8.5 mM, NaCl: 120 mM, KCl: 5.4 mM, $CaCl_2$:1.2 mM, $MgSO_4$:1.2 mM and glucose: 10 mM. The cells were harvested, centrifuged at 125 g for 5 min, washed twice with the Tris-Hepes buffer and diluted to 1,250,000 cells/ml. The intact cell suspension (0.2 ml) was preincubated in triplicate with various drug dilutions for 15 min. Dopamine transport was initiated by the addition of [$^3$H]dopamine (0.2 ml; DuPont-NEN, Boston, Mass.) for 10 min, at 25° C. The specific activity of the radioactive dopamine was 27.5 Ci/mM. Transport was terminated by filtration (Brandel, Gaithersburg, Md.) and two rapid washes with 5 ml of cold Tris-Hepes buffer over GF/B glass fiber filters (Whatman, Maidstone, UK) presoaked in 0.1% polyethylenimine (Sigma, St-Louis, Mo.). Bound radioactivity was measured by liquid scintillation (Wallac, Gaithersburg, Md.) spectrometry (LS60001C, Beckman, Fullerton, Calif.). Nonspecific uptake was defined as the uptake in the presence of 30 TM (–) cocaine, and these data were subtracted from total counts to yield specific accumulation of [$^3$H]dopamine. The experiments were performed in triplicate and each value is the mean±S.E. of 2–5 independent experiments. Protein concentrations were determined by Bradford assay (Bio-Rad, Richmond, Calif.).

Affinities of Drugs for the Dopamine Transporter, Labeled with [³H]CFT in HEK-293 Cells Expressing the Human Dopamine Transporter.

Similar intact cell suspension (0.2 ml) in buffer with tropolone (100 TM) were used for [³H]CFT binding studies. In triplicate, various dilution of drugs (0.2 ml; 10 pM to 10 TM) were incubated with 1 nM [³H]CFT (0.2 ml; 80 Ci/mmol; NEN, Boston, Mass.) for 2 hours, at 4° C. Binding was terminated and measured as described above. Nonspecific binding was defined in the presence of 30 TM (−) cocaine, and these data were subtracted from total counts to yield total counts to yield specific binding of [³H]CFT. The experiments were performed in triplicate and each value is the mean±S.E. of 2–5 independent experiments. Competition analysis of [³H]CFT binding was performed with EBDA and LIGAND computer programs (Elsevier-Biosoft, Cambridge, U.K.)

F. Data Analysis.

Data were analyzed by the EBDA and LIGAND computer software programs (ElsevierBiosoft, U.K.) Final estimates of $IC_{50}$ and nH values were computed by the EBDA program. Baseline values for the individual drugs were established by computer analysis, using the baseline drugs as a guide. The LIGAND program provided final parameter estimates for the affinity of the radioligand (Kd) by iterative non-linear curve-fitting and evaluation of one- or two-component binding models. LIGAND was used to measure the affinity of the radioligands at the dopamine and serotonin transporter. Graphs (not shown) were produced by the computer software program PRISM, using a one- or two-site competition analysis curve.

TABLE 2

Affinity of selected compounds at the dopamine and serotonin transporters

| COMPOUND | DAT $IC_{50}$ (nM) | SERT $IC_{50}$ (nM) | DAT/SERT RATIO |
|---|---|---|---|
| Methylphenidate | 17.2 ± 2.04 | >100,000 | 5,800 |
| 0-1730 (threo diastereomer) | 29.1 ± 5.05 | 2,180 ± 226 | 75 |
| 0-1731 (erythro diastereomer) | 286 ± 10.5 | 7,795 ± 1,840 | 27 |
| 0-1783; 2b | 17 ± 1.3 | >10,000 | >588 |
| 0-1792; 1b | 193 ± 3.5 | >10,000 | >50 |
| 0-1793; 1a | 736 ± 59 | >10,000 | >10 |
| 0-1794; 2a | 33.9 ± 8.6 | 1,655 ± 317 | 49 |
| Indatraline | 2.37 ± 0.11 | — | — |
| 0-1630 Trans-geometry [3,4Cl₂Ph] | 60 ± 23 | 334 ± 100 | 6 |
| 0-1618 | 104 ± 30.8 | >3,000 | >28 |
| 0-1629 | 116 ± 21 | >3,400 | >26 |
| 0-1617 Cis-geometry; [3,4Cl₂Ph] | 130 ± 49.7 | >4,100 | >32 |
| 0-1833 Cis-geometry [2-Naphthyl] | 189 ± 12 | 422 ± 38 | 2 |
| 0-1925 Trans-geometry [2-Naphthyl] | 213 ± 27 | 136 ± 4.5 | 0.6 |
| O-2075 | 118 | 6,650 | 56 |
| O-2078 | 104 | 2,480 | 24 |
| O-2076 | 70 | >5000 | >70 |
| O-2089 | 755 | >10,000 | >13 |
| O-2098 | 25 | 1,400 | 56 |
| Naphthyl mixture (12) | 300 | 5,000 | 16.7 |
| 8 | 127 | 8,000 | 63 |
| 9 | 146 | 12,000 | 82.2 |
| 10 | 128 | 10,000 | 78 |
| 11 | 47 | 7,000 | 149 |

The naphthyl compound 12, which is the analog of compound 1 and 2, has an $IC_{50}$ of 300 nM. The carbocyclic analogs show surprising potency. The cyclohexyl analogs, as either a methyl ester, 9, or a nitrile, 8, exhibit similar binding potency at the DAT ($IC_{50}$=127–146 nM) and SERT ($IC_{50}$=8–12 μM). While the cyclohexyl nitrile analog 10 is similarly potent ($IC_{50}$=128 nM), the methyl ester 11 manifests substantial binding potency at the DAT ($IC_{50}$=47 nM) with substantial selectivity (150-fold) over the SERT.

A number of embodiments of the invention have been described. Nevertheless, it will be understood that various modifications may be made without departing from the spirit and scope of the invention. Accordingly, other embodiments are within the scope of the following claims.

What is claimed is:

1. A compound having the formula:

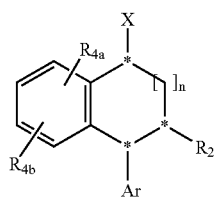

WHERE:
* indicates a chiral center, and each chiral center, independently, may be R, S, or R/S;
—X=—$CH_2R_1$; —$CHR_1R_5$; —$CR_1$=O; —$CR_6$=O; —O—$R_1$; —$SR_1$; —$SOR_6$; —$SO_2R_6$; —$SO_2NHR_1$; or —CH=$CR_1R_5$ and where:
 a. —$R_1$ and —$R_5$ are independently selected from: —H; —$CH_3$; —$CH_2CH_3$; or —$CH_2(CH_2)_mCH_3$, where m=0, 1, 2, or 3;
 PROVIDED THAT, when X=—O—$R_1$, then $R_1 \neq H$; and
 b. —$R_6$ is selected from: —OH; —$OCH_3$; —$NHR_1$; —O-alkyl; —O-alkenyl; —O-alkynyl; —O-allyl; —O-iodoallyl; -alkyl; -alkenyl; -alkynyl; -allyl; -isopropyl; and -isobutyl;
—Ar=
 phenyl substituted at any two positions with $R_{3a}$ and $R_{3b}$, where $R_{3a}$ and $R_{3b}$ are as defined in options "I." or "II.", below;
 OPTION I. for $R_{3a}$ and $R_{3b}$
  —$R_{3a}$ and —$R_{3b}$ are independently selected from: —H; —Br; —Cl; —I; —F; —OH; —$OCH_3$; —$CF_3$; —$NO_2$; —$NH_2$; —CN; —$NHCOCH_3$; —$C(CH_3)_3$; —$(CH_2)_qCH_3$ where q=0–6; —$COCH_3$; —F (at the 2, 3 or 4 position), —Cl (at the 2, 3 or 4 position); —I (at the 2, 3 or 4 position); alkyl; alkenyl; alkynyl; allyl; iospropyl; isobutyl; alkyl; -alkyl$N_2S_2$chelator; -alkyl$N_2S_2$Tc chelator; or $COR_7$, where $R_7$ is defined below; or
 OPTION II. for $R_{3a}$ and $R_{3b}$
  —$R_{3a}$ and —$R_{3b}$ as a pair are independently selected from the following pairs: 3,4-diCl; 3,4, diOH; 3,4-diOAc; 3,4-$diOCH_3$; 3-OH, 4-Cl; 3-OH,4-F; 3-Cl,4-OH; or 3-F,4-OH;
n=0 or 1;
—$R_2$=—H; —$COOCH_3$; —$COR_7$; -alkyl; -alkenyl; -allyl; -iodoallyl; -alkynyl; -alkyl$N_2S_2$ chelator-; —O-alkyl$N_2S_2$ chelator; -alkyl$N_2S_2$Tc chelator; —O-alkyl$N_2S_2$Tc chelator; where,
 —$R_7$ is=—$NHR_8$; morpholinyl; piperidinyl; —$CH_3$; —$CH_2CH_3$; —$CH_2(CH_2)_rCH_3$ where r=0, 1, 2, or 3; alkyl; alkenyl; alkynyl; allyl; isopropyl; iodoallyl; O-iodoallyl; -isobutyl; —$CH_2SO_2$; -alkyl$N_2S_2$ chelator; -alkylN₂S₂Tc chelator; O-alkylN₂S₂ chelator; or —O-alkylN₂S₂Tc chelator; and —R₈ is=-alkyl; -alkenyl; -allyl; -iodoallyl; -alkynyl; -isoxazole; -oxadiazole; -oxazole; -alkylN₂S₂ chelator —O-alkylN₂S₂ chelator; -alkylN₂S₂Tc chelator; or —O-alkylN₂S₂Tc chelator;

R4a and R4b are independently selected from:
—H; —Br; —Cl; —I; —F; —OH; —OCH₃; —CF₃; —NO₂; —NH₂; —CN; —NHCOCH₃, —C(CH₃)₃, —(CH₂)$_q$CH₃ where q=0–6; —COCH₃; —F (at the 2, 3 or 4 position), —Cl (at the 2, 3 or 4 position); —I (at the 2, 3 or 4 position); alkyl; alkenyl; alkynyl; allyl; iospropyl; isobutyl; alkyl; -alkylN₂S₂; -alkylN₂S₂Tc; and COR₇, where R₇ is defined above; or R4a and R4b are selected as a pair from the following pairs:
3,4-diCl; 3,4-diOH; 3,4-diOAc; 3,4-diOCH₃; 3-OH, 4-Cl; 3-OH,4-F; 3-Cl,4-OH; and 3-F, 4-OH.

2. The compound of claim 1 in which n=0.

3. The compound of claim 1 or claim 2 in which X=—O—R₁.

4. The compound of claim 3 in which —R₁=—CH₃.

5. The compound of claim 1 in which Ar=phenyl substituted at any two positions with $R_{3a}$, and $R_{3b}$.

6. The compound of claim 5 in which $R_{3a}$, and $R_{3b}$ are independently selected from —H and —Cl.

7. The compound of claim 6 in which $R_{3a}$, and $R_{3b}$ are both —Cl.

8. A compound selected from the group consisting of

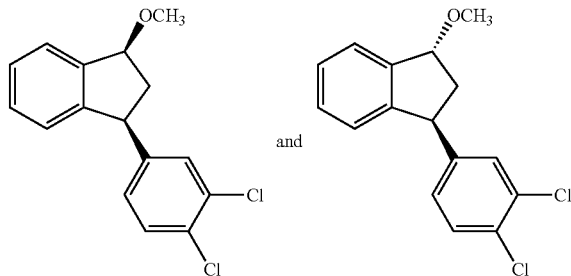

and

9. A pharmaceutical composition comprising a compound according to any one claims 1–4, 5–7 or 8 mixed with a pharmaceutically acceptable carrier.

* * * * *